US008263071B2

(12) United States Patent
Burgess

(10) Patent No.: US 8,263,071 B2
(45) Date of Patent: Sep. 11, 2012

(54) PROTEIN INVOLVED IN OVARIAN CANCER

(75) Inventor: Nicola Anne Burgess, Slough (GB)

(73) Assignee: UCB Pharma S.A., Brussels (BE)

( * ) Notice: Subject to any disclaimer, the term of this patent is extended or adjusted under 35 U.S.C. 154(b) by 279 days.

(21) Appl. No.: 12/587,870

(22) Filed: Oct. 14, 2009

(65) Prior Publication Data

US 2011/0059088 A1   Mar. 10, 2011

Related U.S. Application Data

(63) Continuation of application No. 10/575,311, filed as application No. PCT/GB2004/004502 on Oct. 22, 2004, now abandoned.

(30) Foreign Application Priority Data

Oct. 22, 2003   (GB) .................................. 0324656.8

(51) Int. Cl.
    *A61K 39/395*   (2006.01)
(52) U.S. Cl. .................................. 424/130.1; 424/178.1
(58) Field of Classification Search .................. None
    See application file for complete search history.

(56) References Cited

U.S. PATENT DOCUMENTS

2002/0142003 A1   10/2002   Schweifer et al.
2004/0180002 A1*   9/2004   Young et al. ................. 424/1.49

FOREIGN PATENT DOCUMENTS

| WO | 0006698 | 2/2000 |
|----|---------|--------|
| WO | WO 02/04508 A1 | 1/2002 |
| WO | WO 02/070539 A2 | 9/2002 |
| WO | 2004074481 | 9/2004 |

OTHER PUBLICATIONS

Gura, Science, 1997, 278:1041-1042.*
Kaiser, Science, 2006, 313, 1370.*
White et al, Annu Rev Med 52:125-145, 2001.*
Freshney, Culture of Animal Cells, A Manual of Basic Technique, Alan R. Liss, Inc., 1983, New York, p. 4.*
Dermer, Bio/Technology, 1994, 12:320.*
Zips et al, in Vivo, 2005, 19:1-7.*
Rudikoff, et al. Proc Natl Acad Sci USA, 1982. vol. 79, p. 1979.*
Colman P. M., Research in Immunology, 145:33-36, 1994.*
MacCallum et al, J. Mol. Biol., 262, 732-745, 1996.*
Pascalis et al, Journal of Immunology, 2002, vol. 169, pp. 3076-3084.*
Casset et al, Biochemical and Biophysical Research Communications, 2003, vol. 307, pp. 198-205.*
Vajdos et al, Journal of Molecular Biology, 2002, vol. 320, pp. 415-428.*
Burgess, et al., Journal of Cell Biology, 1990. vol. 111, pp. 2129-2138.*
Schwartz. et al., Proc Natl Acad Sci USA, 1987. vol. 84, pp. 6408-6411.*
Lin, et al. Biochemistry USA, 1975. vol. 14 pp. 1559-1563).*
T. Conze et al., CDCP1 is a Novel Marker for Hematopoietic Stem Cells, Annals New York Academy of Sciences, 996:222-226 (2003).
M. Scherl-Mostageer et al., Identification of a novel gene, CDCP1, overexpressed in human colorectal cancer, Oncogene, 20:4402-4408 (2001).
J.D. Hooper et al., Subtractive immunization using highly metastatic human tumor cells identifies SIMA135/CDCP1, a 135 kDa cell surface phosphorylated glycoprotein antigen, Oncogene, 22:1783-1794 (2003).
Brown, et al., "Adhesion or Plasmin Regulates Tyrosine Phosphorylation of a Novel membrane Glycoprotein p80/gp140/CUB Domain-containing Protein 1 in Epithelia", Journal of Biological Chemistry, 2004; 15: 14722-14783.
Buhring, et al., "CDCPI Identifies a Broad Spectrum of Normal and Malignant Stem/Progenitor Cell Subsets of Hematopoietic and Nonhematopoietic Origin", Stem Cells, 2004; 22: 334-343.

* cited by examiner

*Primary Examiner* — Peter J Reddig
*Assistant Examiner* — Mark Halvorson
(74) *Attorney, Agent, or Firm* — Klauber & Jackson LLC

(57) ABSTRACT

The present invention relates to new uses of CDCP1 in the diagnosis, screening, treatment and prophylaxis of ovarian cancer. The invention also provides compositions comprising CDCP1, including vaccines, antibodies that are immunospecific for CDCP1 and agents which interact with or modulate the expression or activity of CDCP1 or which modulate the expression of the nucleic acid which codes for CDCP1.

3 Claims, 5 Drawing Sheets

Figure 3:
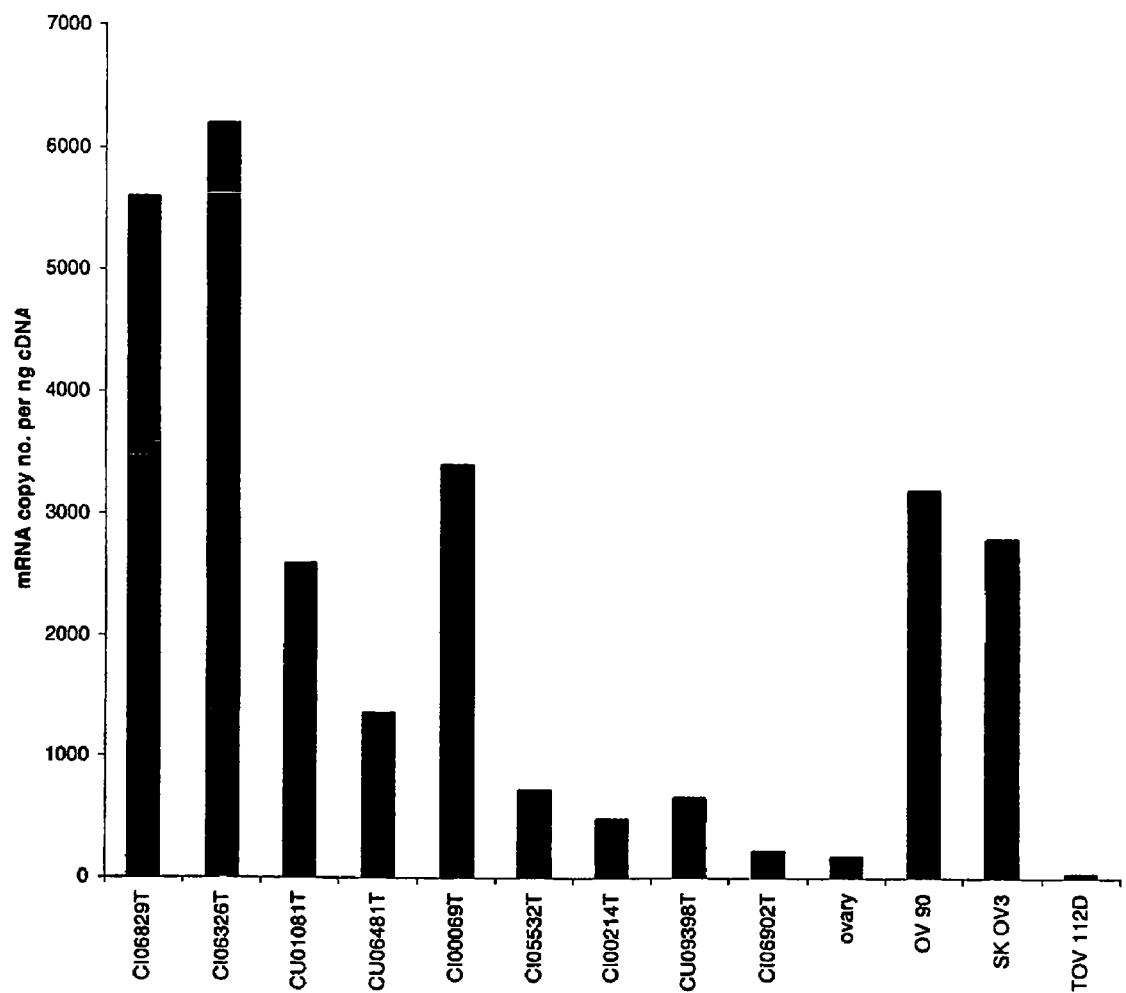

```
  1 MAGLNCGVSI ALLGVLLLGA ARLPRGAEAF EIALPRESNI TVLIKLGTPT LLAKPCYIVI
 61 SKRHITMLSI KSGERIVFTF SCQSPENHFV IEIQKNIDCM SGPCPFGEVQ LQPSTSLLPT
121 LNRTFIWDVK AHKSIGLELQ FSIPRLRQIG PGESCPDGVT HSISGRIDAT VVRIGTFCSN
181 GTVSRIKMQE GVKMALHLPW FHPRNVSGFS IANRSSIKRL CIIESVFEGE GSATLMSANY
241 PEGFPEDELM TWQFVVPAHL RASVSFLNFN LSNCERKEER VEYYIPGSTT NPEVFKLEDK
301 QPGNMAGNFN LSLQGCDQDA QSPGILRLQF QVLVQHPQNE SNKIYVVDLS NERAMSLTIE
361 PRPVKQSRKF VPGCFVCLES RTCSSNLTLT SGSKHKISFL CDDLTRLWMN VEKTISCTDH
421 RYCQRKSYSL QVPSDILHLP VELHDFSWKL LVPKDRLSLV LVPAQKLQQH THEKPCNTSF
481 SYLVASAIPS QDLYFGSFCP GGSIKQIQVK QNISVTLRTF APSFRQEASR QGLTVSFIPY
541 FKEEGVFTVT PDTKSKVYLR TPNWDRGLPS LTSVSWNISV PRDQVACLTF FKERSGVVCQ
601 TGRAFMIIQE QRTRAEEIFS LDEDVLPKPS FHHHSFWVNI SNCSPTSGKQ LDLLFSVTLT
661 PRTVDLTVIL IAAVGGVLL LSALGLIICC VKKKKKKTNK GPAVGIYNGN INTEMPRQPK
721 KFQKGRKDND SHVYAVIEDT MVYGHLLQDS SGSFLQPEVD TYRPFQGTMG VCPPSPPTIC
781 SRAPTAKLAT EEPPPRSPPE SESEPYTFSH PNNGDVSSKD TDIPLLSTQE PMEPAE
```

Figure 1

```
   1 gcgcgcaggt gagtgagcca gggcggagcg cagctgcgcc gggcttgggc gcctggggcc
  61 gccgctcccc accgtcgttt tccccaccga ggccgaggcg tcccggagtc atggccggcc
 121 tgaactgcgg ggtctctatc gcactgctag gggttctgct gctgggtgcg gcgcgcctgc
 181 cgcgcggggc agaagctttt gagattgctc tgccacgaga aagcaacatt acagttctca
 241 taaagctggg gaccccgact ctgctggcaa acccctgtta catcgtcatt tctaaaagac
 301 atataaccat gttgtccatc aagtctggag aaagaatagt ctttaccttt agctgccaga
 361 gtcctgagaa tcactttgtc atagagatcc agaaaaatat tgactgtatg tcaggcccat
 421 gtcctttttgg ggaggttcag cttcagccct cgacatcgtt gttgcctacc ctcaacagaa
 481 ctttcatctg ggatgtcaaa gctcataaga gcatcggttt agagctgcag ttttccatcc
 541 ctcgcctgag gcagatcggt ccgggtgaga gctgcccaga cggagtcact cactccatca
 601 gcggccgaat cgatgccacc gtggtcagga tcggaacctt ctgcagcaat ggcactgtgt
 661 cccggatcaa gatgcaagaa ggagtgaaaa tggccttaca cctcccatgg ttccacccca
 721 gaaatgtctc cggcttcagc attgcaaacc gctcatctat aaaacgtctg tgcatcatcg
 781 agtctgtgtt tgagggtgaa ggctcagcaa ccctgatgtc tgccaactac ccagaaggct
 841 tccctgagga tgagctcatg acgtggcagt tgtcgttcc tgcacacctg cgggccagcg
 901 tctccttcct caacttcaac ctctccaact gtgagaggaa ggaggagcgg gttgaatact
 961 acatcccggg ctccaccacc aaccccgagg tgttcaagct ggaggacaag cagcctggga
1021 acatggcggg gaacttcaac ctctctctgc aaggctgtga ccaagatgcc caaagtccag
1081 ggatcctccg gctgcagttc caagttttgg tccaacatcc acaaaatgaa agcaataaaa
1141 tctacgtggt tgacttgagt aatgagcgag ccatgtcact caccatcgag ccacggcccg
1201 tcaaacagag ccgcaagttt gtccctggct gtttcgtgtg tctagaatct cggacctgca
1261 gtagcaacct caccctgaca tctggctcca aacacaaaat ctccttcctt tgtgatgatc
1321 tgacacgtct gtggatgaat gtggaaaaaa ccataagctg cacagaccac cggtactgcc
1381 aaaggaaatc ctactcactc caggtgccca gtgacatcct ccacctgcct gtggagctgc
1441 atgacttctc ctggaagctg ctggtgccca aggacaggct cagcctggtg ctggtgccag
1501 cccagaagct gcagcagcat acacacgaga agccctgcaa caccagcttc agctacctcg
1561 tggccagtgc catacccagc caggacctgt acttcggctc cttctgcccg ggaggctcta
1621 tcaagcagat ccaggtgaag cagaacatct cggtgaccct tcgcaccttt gccccagct
1681 tccgacaaga ggcctccagg cagggtctga cggtgtcctt tatccttat ttcaaagagg
1741 aaggcgtttt cacggtgacc cctgacacaa aaagcaaggt ctacctgagg acccccaact
1801 gggaccgggg cctgccatcc ctcacctctg tgtcctggaa catcagtgtg cccagagacc
1861 aggtggcctg cctgactttc tttaaggagc ggagcggcgt ggtctgccag acagggcgcg
1921 cattcatgat catccaggag cagcggaccc gggctgagga gatcttcagc ctggacgagg
1981 atgtgctccc caagccaagc ttccaccatc acagcttctg ggtcaacatc tctaactgca
```

Figure 2

```
2041 gccccacgag cggcaagcag ctagacctgc tcttctcggt gacacttacc ccaaggactg
2101 tggacttgac tgtcatcctc atcgcagcgg tgggaggtgg agtcttactg ctgtctgccc
2161 tcgggctcat catttgctgt gtgaaaaaga agaaaaagaa gacaaacaag ggccccgctg
2221 tgggtatcta caatggcaac atcaatactg agatgccgag gcagccaaaa aagtttcaga
2281 aagggcgaaa ggacaatgac tcccatgtgt atgcagtcat cgaggacacc atggtatatg
2341 ggcatctgct acaggattcc agcggctcct tcctgcagcc agaggtggac acctaccggc
2401 cgttccaggg caccatgggg gtctgtcctc cctccccacc caccatatgc tccagggccc
2461 caactgcaaa gttggccact gaggagccac ctcctcgctc ccctcctgag tctgagagtg
2521 aaccgtacac cttctcccat cccaacaatg gggatgtaag cagcaaggac acagacattc
2581 ccttactgag cactcaggag cccatggagc cagcagaata acttgatcca ttccagacgc
2641 tttgctgagt ttcataaagc agggcactga gacaccgtc cgtgttccta accagaaatc
2701 ctaaagaaga ggaattatac agaaggaaca gcaggaggtt ttcctggaca ccgccaactt
2761 cacattgctc agtggactca ttctaagggc aagacattga aaatgatgaa ttccaatctg
2821 gatacagtca tgacagctca tgtgctcctc aacttaggct gtgcggttag ccagcctgta
2881 atgagaggag agaggcctga gtcacctagc atagggttgc agcaagccct ggattcagag
2941 tgttaaacag aggcttgccc tcttcaggac aacagttcca attccaagga gcctacctga
3001 ggtccctact ctcactgggg tccccaggat gaaaacgaca atgtgccttt ttattattat
3061 ttatttggtg gtcctgtgtt atttaagaga tcaaatgtat aaccacctag cacttttcac
3121 ctgacttagt aataactcat actaactggt ttggatgcct gggttgtgac ttctactgac
3181 cgctagataa acgtgtgcct gtcccccagg tggtgggaat aatttacaat ctgtccaacc
3241 agaaaagaat gtgtgtgttt gagcagcatt gacacatatc tgctttgata agagacttcc
3301 tgattctcta ggtcggttcg tggttatccc attgtggaaa ttcatcttga atcccattgt
3361 cctatagtcc tagcaataag agaaatttcc tcaagtttcc atgtgcggtt ctcctagctg
3421 cagcaatact ttgacattta aagagaaatt tagagaatat tctcatcctc taaaaatgtt
3481 taaatatata ccaaacagtg gcccctgca ttagttttct gttgccactg caacctatta
3541 cttggtagct taaaaacaac acattagctt atagtcctgg ggatcagaat tccaaaatgg
3601 atgtccctga atgaaaatca aggtgtcagc agagctgtgc tccttctgaa ggctctaggg
3661 agaagccggt tccttgccat ttcaagcttc tagaggctgg ctgcattccc aggctccagt
3721 ggctggtcaa gcttttctca catggcatca ctgtgacact ggccctccca cttccctctt
3781 tgacttacaa agcccaccag gaagatccag gataatctct ccatctaaag ttccttcatc
3841 atcctggaag agccttttgc catgcaagac aacatagcca caggtgggga ttaggaccag
3901 aacatctttg gggtgctgtt attctgccta ccacaccttc ctgccactga ctcccacagg
3961 agaggctaca aaatgatctg gcgcacaggg atgttttgtt tagcttgcgg actctaacac
4021 ttaaaaaaaa acccagatca gaagatctgg ccatgctggg gctcacattc tcacctagca
4081 acaactggct ggagctgggc accagctctg cctttagaag gggtgtccac ttcaccaggt
```

Figure 2 (Cont'd)

```
4141 caccacagcc cacactacgc cctatcactt cccacaatga ggctgagtgt ttgtttctac
4201 tgatcaatgc cctgcaggt tgcatttatt gtaatgaaaa agaaagactg ggattaatct
4261 ctaatcaggt gagtagacca tgagaccaat gtgtgctcac attcccttt ttcttttt
4321 tcttttctt tttcttttt ttttaatgt gagacaggat ctcattctgt tgcctaggct
4381 ggagtgcagt ggcgcaatct cggctcactg caacctctgc ctcctgggct caagcaattc
4441 tcccacctca gcctcccaaa tagctgggat cactggcaca aaccaccatg cccagctaat
4501 tttgtatttt ttgtagagac agggtttcac catgttgccc aggctggtct caacctcctg
4561 ggctcaagca atcctcctgc ctcggcctcc caaagtgctg ggattacaga tgtgagccac
4621 cgcatccagc cccacaccct catttatacc aattacctgc ccagtaactg tggacttttg
4681 cttcctcacc cctgctctga tctggaagga gagggattat gttatagctt gtcagcacag
4741 tcccaagttc aatatttctg cggcaaaaac ttccttcaaa aaataaatgt acttcattgt
4801 attcaatgaa ttcaccttgg aaatgcaccg cctcaacttg ttcacatggc ataaatgaaa
4861 ggaattttat agtctcctaa atggcgtgta ctgcaagacc tcttgaacac tttccagagg
4921 ataggatatt taagtcatgc ccttgcgtcc tatggcacct ttcccttctg aaagtctggt
4981 tcctgcccag tgaccttgg ccttgtgagc cgagatgctg accctgcata aagggccaaa
5041 ggagggctgc ggcttccttc cctcactgaa gagcccttat ttgaattcac tgtgtggagc
5101 cctagccctc cattctcgac attccccaac ctcccagccc cttccaagca ggactaggtg
5161 ccctgcattc cacccaaggt gggattggcc ttccttaggc tggctacttg tcaccatcac
5221 cgacatcact gttgcctgca aggacaccac gtggccattt tccttcaact gagggctcaa
5281 aactcctgga caagttgctg gctcctgaga ccagtatttc ctggagctgt gcctcagtga
5341 aggggcccag cctgaggaac cctggctctt ttctttaaag cccaggcccc acttacgtaa
5401 aacatttcag ggtcactgga aacagtgaag tgccatttgt tgaagcctac tgcatgccag
5461 cccactgctc atccacgtgg tctgccatgc ctacgaggaa ggccagcgca tgcaggactg
5521 gtctctaatg ctgtggtcat tgcacagaag ggaaaggtct caaggaagag tcaactggaa
5581 caagcacaag cccaccggac atggccttgg taaaggttag cagactggtg tgtgtggatc
5641 tgcagtgctt cactggaaat aatttattca ttgcagatac tttttaggtg gcatttatt
5701 catttcctgt gctttaaata aacaaatgta ccaaaaaaca agtatcaagc tgtttaagtg
5761 cttcggctac ttgtcccctg gttcagtaga ggccccggtt tccagttgt tgactgtgac
5821 aggctcagca tgggctcagc agatgctgtc ttaatttgtg gatgatacag aaagccaggc
5881 tttgggatac aagttctttc ctcttcattt gatgccgtgc actgtgtgaa gcagatgttt
5941 ttgtccggaa ataaaaataa tagtcttgga gtctcgcc
```

Figure 2 (Cont'd)

SEQUENCE LISTING

<160> NUMBER OF SEQ ID NOS: 4

<210> SEQ ID NO 1
<211> LENGTH: 836
<212> TYPE: PRT
<213> ORGANISM: Homo Sapiens

<400> SEQUENCE: 1

```
Met Ala Gly Leu Asn Cys Gly Val Ser Ile Ala Leu Leu Gly Val Leu
1               5                   10                  15

Leu Leu Gly Ala Ala Arg Leu Pro Arg Gly Ala Glu Ala Phe Glu Ile
                20                  25                  30

Ala Leu Pro Arg Glu Ser Asn Ile Thr Val Leu Ile Lys Leu Gly Thr
            35                  40                  45

Pro Thr Leu Leu Ala Lys Pro Cys Tyr Ile Val Ile Ser Lys Arg His
        50                  55                  60

Ile Thr Met Leu Ser Ile Lys Ser Gly Glu Arg Ile Val Phe Thr Phe
65                  70                  75                  80

Ser Cys Gln Ser Pro Glu Asn His Phe Val Ile Glu Ile Gln Lys Asn
                85                  90                  95

Ile Asp Cys Met Ser Gly Pro Cys Pro Phe Gly Glu Val Gln Leu Gln
            100                 105                 110

Pro Ser Thr Ser Leu Leu Pro Thr Leu Asn Arg Thr Phe Ile Trp Asp
        115                 120                 125

Val Lys Ala His Lys Ser Ile Gly Leu Glu Leu Gln Phe Ser Ile Pro
    130                 135                 140

Arg Leu Arg Gln Ile Gly Pro Gly Glu Ser Cys Pro Asp Gly Val Thr
145                 150                 155                 160

His Ser Ile Ser Gly Arg Ile Asp Ala Thr Val Val Arg Ile Gly Thr
                165                 170                 175

Phe Cys Ser Asn Gly Thr Val Ser Arg Ile Lys Met Gln Glu Gly Val
            180                 185                 190
```

-continued

```
Lys Met Ala Leu His Leu Pro Trp Phe His Pro Arg Asn Val Ser Gly
        195                 200                 205
Phe Ser Ile Ala Asn Arg Ser Ser Ile Lys Arg Leu Cys Ile Ile Glu
        210                 215                 220
Ser Val Phe Glu Gly Glu Gly Ser Ala Thr Leu Met Ser Ala Asn Tyr
225                 230                 235                 240
Pro Glu Gly Phe Pro Glu Asp Glu Leu Met Thr Trp Gln Phe Val Val
                245                 250                 255
Pro Ala His Leu Arg Ala Ser Val Ser Phe Leu Asn Phe Asn Leu Ser
            260                 265                 270
Asn Cys Glu Arg Lys Glu Glu Arg Val Glu Tyr Tyr Ile Pro Gly Ser
        275                 280                 285
Thr Thr Asn Pro Glu Val Phe Lys Leu Glu Asp Lys Gln Pro Gly Asn
        290                 295                 300
Met Ala Gly Asn Phe Asn Leu Ser Leu Gln Gly Cys Asp Gln Asp Ala
305                 310                 315                 320
Gln Ser Pro Gly Ile Leu Arg Leu Gln Phe Gln Val Leu Val Gln His
                325                 330                 335
Pro Gln Asn Glu Ser Asn Lys Ile Tyr Val Val Asp Leu Ser Asn Glu
            340                 345                 350
Arg Ala Met Ser Leu Thr Ile Glu Pro Arg Pro Val Lys Gln Ser Arg
        355                 360                 365
Lys Phe Val Pro Gly Cys Phe Val Cys Leu Glu Ser Arg Thr Cys Ser
        370                 375                 380
Ser Asn Leu Thr Leu Thr Ser Gly Ser Lys His Lys Ile Ser Phe Leu
385                 390                 395                 400
Cys Asp Asp Leu Thr Arg Leu Trp Met Asn Val Glu Lys Thr Ile Ser
                405                 410                 415
Cys Thr Asp His Arg Tyr Cys Gln Arg Lys Ser Tyr Ser Leu Gln Val
            420                 425                 430
Pro Ser Asp Ile Leu His Leu Pro Val Glu Leu His Asp Phe Ser Trp
        435                 440                 445
Lys Leu Leu Val Pro Lys Asp Arg Leu Ser Leu Val Leu Val Pro Ala
        450                 455                 460
Gln Lys Leu Gln Gln His Thr His Glu Lys Pro Cys Asn Thr Ser Phe
465                 470                 475                 480
Ser Tyr Leu Val Ala Ser Ala Ile Pro Ser Gln Asp Leu Tyr Phe Gly
                485                 490                 495
Ser Phe Cys Pro Gly Gly Ser Ile Lys Gln Ile Gln Val Lys Gln Asn
            500                 505                 510
Ile Ser Val Thr Leu Arg Thr Phe Ala Pro Ser Phe Arg Gln Glu Ala
        515                 520                 525
Ser Arg Gln Gly Leu Thr Val Ser Phe Ile Pro Tyr Phe Lys Glu Glu
        530                 535                 540
Gly Val Phe Thr Val Thr Pro Asp Thr Lys Ser Lys Val Tyr Leu Arg
545                 550                 555                 560
Thr Pro Asn Trp Asp Arg Gly Leu Pro Ser Leu Thr Ser Val Ser Trp
                565                 570                 575
Asn Ile Ser Val Pro Arg Asp Gln Val Ala Cys Leu Thr Phe Phe Lys
            580                 585                 590
Glu Arg Ser Gly Val Val Cys Gln Thr Gly Arg Ala Phe Met Ile Ile
        595                 600                 605
Gln Glu Gln Arg Thr Arg Ala Glu Glu Ile Phe Ser Leu Asp Glu Asp
```

```
                610                615                620
Val Leu Pro Lys Pro Ser Phe His His Ser Phe Trp Val Asn Ile
625                630                635                640

Ser Asn Cys Ser Pro Thr Ser Gly Lys Gln Leu Asp Leu Leu Phe Ser
                645                650                655

Val Thr Leu Thr Pro Arg Thr Val Asp Leu Thr Val Ile Leu Ile Ala
                660                665                670

Ala Val Gly Gly Val Leu Leu Ser Ala Leu Gly Leu Ile Ile
                675                680                685

Cys Cys Val Lys Lys Lys Lys Lys Thr Asn Lys Gly Pro Ala Val
        690                695                700

Gly Ile Tyr Asn Gly Asn Ile Asn Thr Glu Met Pro Arg Gln Pro Lys
705                710                715                720

Lys Phe Gln Lys Gly Arg Lys Asp Asn Asp Ser His Val Tyr Ala Val
                725                730                735

Ile Glu Asp Thr Met Val Tyr Gly His Leu Leu Gln Asp Ser Ser Gly
                740                745                750

Ser Phe Leu Gln Pro Glu Val Asp Thr Tyr Arg Pro Phe Gln Gly Thr
                755                760                765

Met Gly Val Cys Pro Pro Ser Pro Pro Thr Ile Cys Ser Arg Ala Pro
770                775                780

Thr Ala Lys Leu Ala Thr Glu Glu Pro Pro Arg Ser Pro Pro Glu
785                790                795                800

Ser Glu Ser Glu Pro Tyr Thr Phe Ser His Pro Asn Asn Gly Asp Val
                805                810                815

Ser Ser Lys Asp Thr Asp Ile Pro Leu Leu Ser Thr Gln Glu Pro Met
                820                825                830

Glu Pro Ala Glu
        835

<210> SEQ ID NO 2
<211> LENGTH: 5978
<212> TYPE: DNA
<213> ORGANISM: Homo Sapiens

<400> SEQUENCE: 2
gcgcgcaggt gagtgagcca gggcggagcg cagctgcgcc gggcttgggc gcctggggcc      60
gccgctcccc accgtcgttt tccccaccga ggccgaggcg tcccggagtc atggccggcc     120
tgaactgcgg ggtctctatc gcactgctag gggttctgct gctgggtgcg gcgcgcctgc     180
cgcgcggggc agaagctttt gagattgctc tgccacgaga agcaacatt acagttctca      240 taaagctggg gaccccgact ctgctggcaa accctgttta catcgtcatt tctaaaagac     300
atataaccat gttgtccatc aagtctggag aaagaatagt ctttacctttt agctgccaga    360 gtcctgagaa tcactttgtc atagagatcc agaaaaatat tgactgtatg tcaggcccat     420
gtccttttgg ggaggttcag cttcagccct cgacatcgtt gttgcctacc ctcaacagaa     480
ctttcatctg ggatgtcaaa gctcataaga gcatcggttt agagctgcag ttttccatcc     540
ctcgcctgag gcagatcggt ccgggtgaga gctgcccaga cggagtcact cactccatca     600
gcggccgaat cgatgccacc gtggtcagga tcggaacctt ctgcagcaat ggcactgtgt     660
cccggatcaa gatgcaagaa ggagtgaaaa tggccttaca cctcccatgg ttccacccca     720
gaaatgtctc cggcttcagc attgcaaacc gctcatctat aaaacgtctg tgcatcatcg     780
agtctgtgtt tgagggtgaa ggctcagcaa ccctgatgtc tgccaactac ccagaaggct     840
```

```
tccctgagga tgagctcatg acgtggcagt ttgtcgttcc tgcacacctg cgggccagcg      900
tctccttcct caacttcaac ctctccaact gtgagaggaa ggaggagcgg gttgaatact      960
acatcccggg ctccaccacc aaccccgagg tgttcaagct ggaggacaag cagcctggga     1020
acatggcggg gaacttcaac ctctctctgc aaggctgtga ccaagatgcc caaagtccag     1080
ggatcctccg gctgcagttc caagtttttgg tccaacatcc acaaaatgaa agcaataaaa    1140
tctacgtggt tgacttgagt aatgagcgag ccatgtcact caccatcgag ccacggcccg     1200
tcaaacagag ccgcaagttt gtccctggct gtttcgtgtg tctagaatct cggacctgca     1260
gtagcaacct caccctgaca tctggctcca aacacaaaat ctccttcctt tgtgatgatc     1320
tgacacgtct gtggatgaat gtggaaaaaa ccataagctg cacagaccac cggtactgcc     1380
aaaggaaatc ctactcactc caggtgccca gtgacatcct ccacctgcct gtggagctgc     1440
atgacttctc ctggaagctg ctggtgccca aggacaggct cagcctggtg ctggtgccag     1500
cccagaagct gcagcagcat acacacgaga agccctgcaa caccagcttc agctaccctcg    1560
tggccagtgc catacccagc caggacctgt acttcggctc cttctgcccg ggaggctcta     1620
tcaagcagat ccaggtgaag cagaacatct cggtgaccct tcgcaccttt gcccccagct     1680
tccgacaaga ggcctccagg cagggtctga cggtgtcctt tataccttat ttcaaagagg     1740
aaggcgtttt cacggtgacc cctgacacaa aaagcaaggt ctacctgagg acccccaact     1800
gggaccgggg cctgccatcc ctcacctctg tgtcctggaa catcagtgtg cccagagacc     1860
aggtggcctg cctgactttc tttaaggagc ggagcggcgt ggtctgccag acagggcgcg     1920
cattcatgat catccaggag cagcggaccc gggctgagga gatcttcagc ctggacgagg     1980
atgtgctccc caagccaagc ttccaccatc acagcttctg ggtcaacatc tctaactgca     2040
gccccacgag cggcaagcag ctagacctgc tcttctcggt gacacttacc ccaaggactg     2100
tggacttgac tgtcatcctc atcgcagcgg tgggaggtgg agtcttactg ctgtctgccc     2160
tcgggctcat catttgctgt gtgaaaaaga agaaaaagaa gacaaacaag ggccccgctg     2220
tgggtatcta caatggcaac atcaatactg agatgccgag gcagccaaaa aagtttcaga     2280
aagggcgaaa ggacaatgac tcccatgtgt atgcagtcat cgaggacacc atggtatatg     2340
ggcatctgct acaggattcc agcggctcct tcctgcagcc agaggtggac acctaccggc     2400
cgttccaggg caccatgggg gtctgtcctc cctcccacc caccatatgc tccagggccc      2460
caactgcaaa gttggccact gaggagccac ctcctcgctc ccctcctgag tctgagagtg     2520
aaccgtacac cttctcccat cccaacaatg gggatgtaag cagcaaggac acagacattc     2580
ccttactgag cactcaggag cccatggagc cagcagaata acttgatcca ttccagacgc     2640
tttgctgagt ttcataaagc agggcactga gacacccgtc cgtgttccta accagaaatc     2700
ctaaagaaga ggaattatac agaaggaaca gcaggaggtt ttcctggaca ccgccaactt     2760
cacattgctc agtggactca ttctaagggc aagacattga aaatgatgaa ttccaatctg     2820
gatacagtca tgacagctca tgtgctcctc aacttaggct gtgcggttag ccagcctgta     2880
atgagaggag agaggcctga gtcacctagc atagggttgc agcaagccct ggattcagag     2940
tgttaaacag aggcttgccc tcttcaggac aacagttcca attccaagga gcctacctga     3000
ggtccctact ctcactgggg tccccaggat gaaaacgaca atgtgccttt ttattattat     3060
ttatttggtg gtcctgtgtt atttaagaga tcaaatgtat aaccacctag cacttttcac     3120
ctgacttagt aataactcat actaactggt ttggatgcct gggttgtgac ttctactgac     3180
cgctagataa acgtgtgcct gtcccccagg tggtgggaat aatttacaat ctgtccaacc     3240
```

```
agaaaagaat gtgtgtgttt gagcagcatt gacacatatc tgctttgata agagacttcc   3300
tgattctcta ggtcggttcg tggttatccc attgtggaaa ttcatcttga atcccattgt   3360
cctatagtcc tagcaataag agaaatttcc tcaagtttcc atgtgcggtt ctcctagctg   3420
cagcaatact ttgacattta aagagaaatt tagagaatat tctcatcctc taaaaatgtt   3480
taaatatata ccaaacagtg gcccctgca ttagttttct gttgccactg caacctatta    3540
cttggtagct taaaaacaac acattagctt atagtcctgg ggatcagaat tccaaaatgg   3600
atgtccctga atgaaaatca aggtgtcagc agagctgtgc tccttctgaa ggctctaggg   3660
agaagccggt tccttgccat ttcaagcttc tagaggctgg ctgcattccc aggctccagt   3720
ggctggtcaa gcttttctca catggcatca ctgtgacact ggccctccca cttccctctt   3780
tgacttacaa agcccaccag gaagatccag gataatctct ccatctaaag ttccttcatc   3840
atcctggaag agccttttgc catgcaagac aacatagcca caggtgggga ttaggaccag   3900
aacatctttg gggtgctgtt attctgccta ccacaccttc ctgccactga ctcccacagg   3960
agaggctaca aaatgatctg gcgcacaggg atgttttgtt tagcttgcgg actctaacac   4020
ttaaaaaaaa acccagatca gaagatctgg ccatgctggg gctcacattc tcacctagca   4080
acaactggct ggagctgggc accagctctg cctttagaag gggtgtccac ttcaccaggt   4140
caccacagcc cacactacgc cctatcactt cccacaatga ggctgagtgt ttgtttctac   4200
tgatcaatgc ccctgcaggt tgcatttatt gtaatgaaaa agaaagactg ggattaatct   4260
ctaatcaggt gagtagacca tgagaccaat gtgtgctcac attaccctt ttcttttttt    4320 tctttttctt tttctttttt ttttaatgt gagacaggat ctcattctgt tgcctaggct     4380
ggagtgcagt ggcgcaatct cggctcactg caacctctgc ctcctgggct caagcaattc   4440
tcccacctca gcctcccaaa tagctgggat cactggcaca aaccaccatg cccagctaat   4500
tttgtatttt ttgtagagac agggtttcac catgttgccc aggctggtct caacctcctg   4560
ggctcaagca atcctcctgc ctcggcctcc caaagtgctg ggattacaga tgtgagccac   4620
cgcatccagc cccacaccct catttatacc aattacctgc ccagtaactg tggacttttg   4680
cttcctcacc cctgctctga tctggaagga gagggattat gttatagctt gtcagcacag   4740
tcccaagttc aatatttctg cggcaaaaac ttccttcaaa aaataaatgt acttcattgt   4800
attcaatgaa ttcaccttgg aaatgcaccg cctcaacttg ttcacatggc ataaatgaaa   4860
ggaattttat agtctcctaa atggcgtgta ctgcaagacc tcttgaacac tttccagagg   4920
ataggatatt taagtcatgc ccttgcgtcc tatggcacct ttcccttctg aaagtctggt   4980
tcctgcccag tgacccttgg ccttgtgagc cgagatgctg accctgcata agggccaaa    5040 ggagggctgc ggcttccttc cctcactgaa gagcccttat ttgaattcac tgtgtgggagc  5100 cctagccctc cattctcgac attccccaac ctcccagccc cttccaagca ggactaggtg   5160
ccctgcattc cacccaaggt gggattggcc ttccttaggc tggctacttg tcaccatcac   5220
cgacatcact gttgcctgca aggacaccac gtggccattt tccttcaact gagggctcaa   5280
aactcctgga caagttgctg gctcctgaga ccagtatttc ctggagctgt gcctcagtga   5340
agggccccag cctgaggaac cctggctctt ttctttaaag cccaggcccc acttacgtaa   5400
aacatttcag ggtcactgga aacagtgaag tgccatttgt tgaagcctac tgcatgccag   5460
cccactgctc atccacgtgg tctgccatgc ctacgaggaa ggccagcgca tgcaggactg   5520
gtctctaatg ctgtggtcat tgcacagaag ggaaaggtct caaggaagag tcaactggaa   5580
caagcacaag cccaccggac atggccttgg taaaggttag cagactggtg tgtgtggatc   5640
```

```
tgcagtgctt cactggaaat aatttattca ttgcagatac ttttaggtg gcattttatt    5700 catttcctgt gctttaaata aacaaatgta ccaaaaaaca agtatcaagc tgtttaagtg    5760
cttcggctac ttgtcccctg gttcagtaga ggccccggtt tcccagttgt tgactgtgac    5820
aggctcagca tgggctcagc agatgctgtc ttaatttgtg gatgatacag aaagccaggc    5880
tttgggatac aagttctttc ctcttcattt gatgccgtgc actgtgtgaa gcagatgttt    5940
ttgtccggaa ataaaaataa tagtcttgga gtctcgcc                            5978

<210> SEQ ID NO 3
<211> LENGTH: 22
<212> TYPE: DNA
<213> ORGANISM: Homo Sapiens

<400> SEQUENCE: 3
tcacagaaag gtatccacgc tg                                               22

<210> SEQ ID NO 4
<211> LENGTH: 22
<212> TYPE: DNA
<213> ORGANISM: Homo Sapiens

<400> SEQUENCE: 4
catcctctgc atcattgtac tg                                               22
```

PROTEIN INVOLVED IN OVARIAN CANCER

The present application is a continuation of U.S. Ser. No. 10/575,311 filed on Apr. 11, 2006, now abandoned which is a national stage application claiming the priority of copending PCT Application No. PCT/GB2004/004502, filed Oct. 22, 2004, which in turn claims priority from Great Britain Application Serial No. 0324656.8, filed Oct. 22, 2003. Applicants claim the benefits of 35 U.S.C. §120 as to the PCT application and priority under 35 U.S.C. §119 as to the Great Britain application, and the entire disclosures of all applications are incorporated herein by reference in their entireties.

The present invention relates to methods for the treatment and/or prophylaxis of ovarian cancer comprising targeting of the polypeptide CDCP1, agents which interact with or modulate the expression or activity of the polypeptide, methods for the identification of such agents and the use of CDCP1 in the diagnosis of ovarian cancer.

Ovarian cancer is the deadliest of the gynaecological cancers with around 70% of sufferers with the more common epithelial ovarian cancer initially presenting with late stage disease where the cancer may have spread from the ovaries to other pelvic and abdominal organs or lymph nodes in the pelvis, groin or abdomen (Stage III) or has spread outside to the liver or outside the abdomen, most commonly to the lining around the lungs. The survival rate of such patients is significantly reduced compared to those who present with earlier stage disease. Ovarian cancer has been generally treated with cisplatin-based chemotherapy and often recurs due to acquired cisplatin resistance (Yahata, et al., 2002, *J. Cancer Res. Clin. Oncol.* 128:621-6), hence the need for new drugs and new therapeutic targets. There is also a need for new markers of ovarian cancer as current markers lack adequate sensitivity and specificity to be applicable in large populations (Rai, et al., 2002, *Arch. Pathol. Lab. Med.* 126:1518-26).

Thus, important needs exist for new therapeutic agents for the treatment of ovarian cancer. Additionally, there is a clear need to identify new ovarian cancer-associated proteins for use as sensitive and specific biomarkers for the diagnosis of ovarian cancer in living subjects.

A nucleic acid encoding a polypeptide which shares 834 amino acids out of 836 amino acids with CDCP1 is disclosed in WO 02/70539, US2002/0142003 and WO 02/04508, the latter two of which disclose a potential involvement of that polypeptide in lung and colon cancers.

The present invention is based on the finding that CDCP1 represents a novel therapeutic target for the treatment and/or prophylaxis of ovarian cancer.

Accordingly, the invention provides a method for the treatment and/or prophylaxis of ovarian cancer comprising administering a therapeutically effective amount of an agent which interacts with or modulates the expression or activity of a CDCP1 polypeptide.

A CDCP1 polypeptide includes a polypeptide which:

(a) comprises or consists of the amino acid sequence of SEQ ID NO:1; or (b) is a derivative having one or more amino acid substitutions, modifications, deletions or insertions relative to the amino acid sequence of SEQ ID NO:1 which retains the activity of CDCP1.

The term "polypeptides" includes peptides, polypeptides and proteins. These are used interchangeably unless otherwise specified.

Agents of use in the methods of the invention include without limitation, agents that are capable of interacting with (e.g. binding to, or recognising) a CDCP1 polypeptide or a nucleic acid molecule encoding a CDCP1 polypeptide, or are capable of modulating the interaction, expression, activity of a CDCP1 polypeptide or the expression of a nucleic acid molecule encoding a CDCP1 polypeptide. Such agents include, without limitation, antibodies, nucleic acids (e.g. DNA and RNA), carbohydrates, lipids, proteins, polypeptides, peptides, peptidomimetics, small molecules and other drugs.

Thus, the invention also provides the use of an agent, which interacts with or modulates the expression or activity of a CDCP1 polypeptide for the manufacture of a medicament for the treatment and/or prophylaxis of ovarian cancer.

Most preferably, the agent for use in the treatment and/or prophylaxis of ovarian cancer is an antibody that interacts with (i.e. binds to or recognises) or modulates the activity of a CDCP1 polypeptide. Accordingly, there is provided the use of an antibody that interacts with a CDCP1 polypeptide for use in the manufacture of a medicament for use in the treatment and/or prophylaxis of ovarian cancer. Also provided is a method of treatment and/or prophylaxis of ovarian cancer in a subject comprising administering to said subject a therapeutically effective amount of an antibody that interacts with CDCP1. In one embodiment, an antibody that interacts with a CDCP1 polypeptide may be used to mediate antibody dependent cell cytotoxicity (ADCC) and complement dependent cytotoxicity (CDC). In such a case the antibody is preferably a full length naked antibody. In another aspect of the invention, an antibody that interacts with CDCP1 polypeptides may be used to inhibit the activity of said polypeptides.

Most preferred are antibodies that specifically interact with a CDCP1 polypeptide. Specifically interacting with (e.g. recognising or binding to) means that the antibodies have a greater affinity for CDCP1 polypeptides than for other polypeptides.

An antibody, optionally conjugated to a therapeutic moiety, can be used therapeutically alone or in combination with a cytotoxic factor(s) and/or cytokine(s). In particular, CDCP1 antibodies can be conjugated to a therapeutic agent, such as a cytotoxic agent, a radionuclide or drug moiety to modify a given biological response. The therapeutic agent is not to be construed as limited to classical chemical therapeutic agents. For example, the therapeutic agent may be a drug moiety which may be a protein or polypeptide possessing a desired biological activity. Such moieties may include, for example and without limitation, a toxin such as abrin, ricin A, pseudomonas exotoxin, or diphtheria toxin, a protein such as tumour necrosis factor, α-interferon, β-interferon, nerve growth factor, platelet derived growth factor or tissue plasminogen activator, a thrombotic agent or an anti-angiogenic agent, e.g. angiostatin or endostatin, or, a biological response modifier such as a lymphokine, interleukin-1 (IL-1), interleukin-2 interleukin-6 (IL-6), granulocyte macrophage colony stimulating factor (GM-CSF), granulocyte colony stimulating factor (G-CSF), nerve growth factor (NGF) or other growth factor.

Therapeutic agents also include cytotoxins or cytotoxic agents including any agent that is detrimental to (e.g. kills) cells. Examples include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents also include, but are not limited to, antimetabolites (e.g. methotrexate, 6-mercaptopurine, 6-thioguanine, cytarabine, 5-fluorouracil decarbazine), alkylating agents (e.g. mechlorethamine, thioepa chlorambucil, melphalan, carmustine (BSNU) and lomustine (CCNU), cyclophosphamide, busulfan, dibromomannitol, streptozotocin, mitomycin C, and cis-dichlorodiamine platinum (II) (DDP) cisplatin), anthracyclines (e.g. daunorubicin (formerly daunomycin) and doxorubicin), antibiotics (e.g. dactinomycin (formerly actinomycin), bleomycin, mithramycin, anthramycin (AMC), calicheamicins or duocarmycins), and anti-mitotic agents (e.g. vincristine and vinblastine).

Other therapeutic moieties may include radionuclides such as $^{111}$In and $^{90}$Y, Lu$^{177}$, Bismuth$^{213}$, Californium$^{252}$, Iridium$^{192}$ and Tunsten$^{188}$/Rhenium$^{188}$; or drugs such as but not limited to, alkylphosphocholines, topoisomerase I inhibitors, taxoids and suramin.

Techniques for conjugating such therapeutic agents to antibodies are well known in the art (see, e.g. Arnon et al., "Monoclonal Antibodies For Immunotargeting Of Drugs In Cancer Therapy", in *Monoclonal Antibodies And Cancer Therapy*, Reisfeld et al., eds., 1985 pp. 243-56, ed. Alan R. Liss, Inc; Hellstrom et al., "Antibodies For Drug Delivery", in *Controlled Drug Delivery*, 2nd Ed., Robinson et al., eds., 1987, pp. 623-53, Marcel Dekker, Inc.; Thorpe, "Antibody Carriers Of Cytotoxic Agents In Cancer Therapy: A Review", in *Monoclonal Antibodies '84: Biological And Clinical Applications*; Pinchera et al., 1985, eds., pp. 475-506; "Analysis, Results, And Future Prospective Of The Therapeutic Use Of Radiolabelled Antibody In Cancer Therapy", in *Monoclonal Antibodies For Cancer Detection And Therapy*, Baldwin et al. (eds.), 1985, pp. 303-16, *Academic Press*; Thorpe et al., 1982 "The Preparation And Cytotoxic Properties Of Antibody-Toxin Conjugates", *Immunol. Rev.*, 62:119-58 and Dubowchik et al., 1999, *Pharmacology and Therapeutics*, 83, 67-123).

The antibodies for use in the invention include analogues and derivatives that are modified, for example but without limitation, by the covalent attachment of any type of molecule. Preferably, said attachment does not impair immunospecific binding. In one aspect, an antibody can be conjugated to a second antibody to form an antibody heteroconjugate (see U.S. Pat. No. 4,676,980).

In other embodiments, the invention provides the therapeutic use of fusion proteins of the antibodies (or functionally active fragments thereof), for example but without limitation, where the antibody or fragment thereof is fused via a covalent bond (e.g. a peptide bond), at optionally the N-terminus or the C-terminus, to an amino acid sequence of another protein (or portion thereof; preferably at least a 10, 20 or 50 amino acid portion of the protein). Preferably the antibody, or fragment thereof, is linked to the other protein at the N-terminus of the constant domain of the antibody. In another aspect, an antibody fusion protein may facilitate depletion or purification of a polypeptide as described herein, increase half-life in vivo, and enhance the delivery of an antigen across an epithelial barrier to the immune system.

Where the fusion protein is an antibody fragment linked to an effector or reporter molecule, this may be prepared by standard chemical or recombinant DNA procedures. A preferred effector group is a polymer molecule, which may be attached to the modified Fab fragment to increase its half-life in vivo.

The polymer molecule may, in general, be a synthetic or a naturally occurring polymer, for example an optionally substituted straight or branched chain polyalkylene, polyalkenylene or polyoxyalkylene polymer or a branched or unbranched polysaccharide, e.g. a homo- or hetero-polysaccharide.

Particular optional substituents which may be present on the above-mentioned synthetic polymers include one or more hydroxy, methyl or methoxy groups. Particular examples of synthetic polymers include optionally substituted straight or branched chain poly(ethyleneglycol), poly(propyleneglycol) poly(vinylalcohol) or derivatives thereof, especially optionally substituted poly(ethyleneglycol) such as methoxypoly(ethyleneglycol) or derivatives thereof.

Particular naturally occurring polymers include lactose, amylose, dextran, glycogen or derivatives thereof.

"Derivatives" as used herein is intended to include reactive derivatives, for example thiol-selective reactive groups such as maleimides and the like. The reactive group may be linked directly or through a linker segment to the polymer. It will be appreciated that the residue of such a group will in some instances form part of the product as the linking group between the antibody fragment and the polymer.

The size of the polymer may be varied as desired, but will generally be in an average molecular weight range from 500 Da to 50000 Da, preferably from 5000 to 40000 Da and more preferably from 25000 to 40000 Da. The polymer size may in particular be selected on the basis of the intended use of the product. Thus, for example, where the product is intended to leave the circulation and penetrate tissue, for example for use in the treatment of a tumour, it may be advantageous to use a small molecular weight polymer, for example with a molecular weight of around 5000 Da. For applications where the product remains in the circulation, it may be advantageous to use a higher molecular weight polymer, for example having a molecular weight in the range from 25000 Da to 40000 Da.

Particularly preferred polymers include a polyalkylene polymer, such as a poly(ethyleneglycol) or, especially, a methoxypoly(ethyleneglycol) or a derivative thereof, and especially with a molecular weight in the range from about 25000 Da to about 40000 Da.

Each polymer molecule attached to the modified antibody fragment may be covalently linked to the sulphur atom of a cysteine residue located in the fragment. The covalent linkage will generally be a disulphide bond or, in particular, a sulphur-carbon bond.

Where desired, the antibody fragment may have one or more effector or reporter molecules attached to it. The effector or reporter molecules may be attached to the antibody fragment through any available amino acid side-chain or terminal amino acid functional group located in the fragment, for example any free amino, imino, hydroxyl or carboxyl group.

An activated polymer may be used as the starting material in the preparation of polymer-modified antibody fragments as described above. The activated polymer may be any polymer containing a thiol reactive group such as an α-halocarboxylic acid or ester, e.g. iodoacetamide, an imide, e.g. maleimide, a vinyl sulphone or a disulphide. Such starting materials may be obtained commercially (for example from Nektar Therapeutics, Inc (Huntsville, Ala.), or may be prepared from commercially available starting materials using conventional chemical procedures.

Standard chemical or recombinant DNA procedures in which the antibody fragment is linked either directly or via a coupling agent to the effector or reporter molecule either before or after reaction with the activated polymer as appropriate may be used. Particular chemical procedures include, for example, those described in WO 93/06231, WO 92/22583, WO 90/09195, WO 89/01476, WO 99/15549 and WO 03/031581. Alternatively, where the effector or reporter molecule is a protein or polypeptide the linkage may be achieved using recombinant DNA procedures, for example as described in WO 86/01533 and EP 0392745.

Most preferably antibodies are attached to poly(ethyleneglycol) (PEG) moieties. Preferably, a modified Fab fragment is PEGylated, i.e. has PEG (poly(ethyleneglycol)) covalently attached thereto, e.g. according to the method disclosed in EP 0948544 [see also "Poly(ethyleneglycol) Chemistry, Biotechnical and Biomedical Applications", 1992, J. Milton Harris (ed), Plenum Press, New York, "Poly(ethyleneglycol) Chemistry and Biological Applications", 1997, J. Milton Harris and S. Zalipsky (eds), American Chemical Society, Washington D.C. and "Bioconjugation Protein Coupling Techniques for the Biomedical Sciences", 1998, Aslam, et al., Grove Publishers, New York; Chapman, 2002, *Advanced Drug Delivery Reviews* 2002, 54:531-545]. In one embodiment, a PEG modified Fab fragment has a maleimide group covalently linked to a single thiol group in a modified hinge region. A lysine residue may be covalently linked to the maleimide group. To each of the amine groups on the lysine residue may be attached a methoxypoly(ethyleneglycol) polymer having a molecular weight of approximately 20,000 Da. The total molecular weight of the entire effector molecule may therefore be approximately 40,000 Da.

CDCP1 polypeptides or cells expressing said polypeptides can be used to produce antibodies, e.g. which specifically recognise said CDCP1 polypeptides. Antibodies generated against a CDCP1 polypeptide may be obtained by administering the polypeptides to an animal, preferably a non-human animal, using well-known and routine protocols.

Anti-CDCP1 antibodies include functionally active fragments, derivatives or analogues and may be, but are not limited to, polyclonal, monoclonal, bi-, tri- or tetra-valent antibodies, humanized or chimeric antibodies, single chain antibodies, Fab fragments, Fab' and Fab'$_2$ fragments, fragments produced by a Fab expression library, anti-idiotypic (anti-Id) antibodies, and epitope-binding fragments of any of the above. Humanized antibodies are antibody molecules from non-human species having one or more complementarity determining regions (CDRs) from the non-human species and a framework region from a human immunoglobulin molecule (see, e.g. U.S. Pat. No. 5,585,089). Antibodies include immunoglobulin molecules and immunologically active portions of immunoglobulin molecules, i.e. molecules that contain an antigen binding site that specifically binds an antigen. The immunoglobulin molecules of the invention can be of any class (e.g. IgG, IgE, IgM, IgD and IgA) or subclass of immunoglobulin molecule.

Monoclonal antibodies may be prepared by any method known in the art such as the hybridoma technique (Kohler, et al., 1975, *Nature*, 256:495-497), the trioma technique, the human B-cell hybridoma technique (Kozbor et al., 1983, *Immunology Today*, 4:72) and the EBV-hybridoma technique (Cole et al., *Monoclonal Antibodies and Cancer Therapy*, pp 77-96, Alan R Liss, Inc., 1985).

Chimeric antibodies are those antibodies encoded by immunoglobulin genes that have been genetically engineered so that the light and heavy chain genes are composed of immunoglobulin gene segments belonging to different species. These chimeric antibodies are likely to be less antigenic. Bivalent antibodies may be made by methods known in the art (Milstein et al., 1983, Nature 305:537-539; WO 93/08829, Traunecker et al., 1991, *EMBO J.* 10:3655-3659). Bi-, tri- and tetra-valent antibodies may comprise multiple specificities or may be monospecific (see for example WO 92/22853).

The antibodies for use in the invention may be generated using single lymphocyte antibody methods based on the molecular cloning and expression of immunoglobulin variable region cDNAs generated from single lymphocytes that were selected for the production of specific antibodies such as described by Babcook, et al., 1996, *Proc. Natl. Acad. Sci. USA* 93(15):7843-7848 and in WO92/02551.

The antibodies for use in the present invention can also be generated using various phage display methods known in the art and include those disclosed by Brinkman et al. (in *J. Immunol. Methods,* 1995, 182: 41-50), Ames et al. (*J. Immunol. Methods,* 1995, 184:177-186), Kettleborough et al. (*Eur. J. Immunol.* 1994, 24:952-958), Persic et al. (*Gene,* 1997 187 9-18), Burton et al. (*Advances in Immunology,* 1994, 57:191-280) and WO 90/02809; WO 91/10737; WO 92/01047; WO 92/18619; WO 93/11236; WO 95/15982; WO 95/20401; and U.S. Pat. Nos. 5,698,426; 5,223,409; 5,403,484; 5,580,717; 5,427,908; 5,750,753; 5,821,047; 5,571,698; 5,427,908; 5,516,637; 5,780,225; 5,658,727; 5,733,743 and 5,969,108. Techniques for the production of single chain antibodies, such as those described in U.S. Pat. No. 4,946,778 can also be adapted to produce single chain antibodies to CDCP1 polypeptides. Also, transgenic mice, or other organisms, including other mammals, may be used to express humanized antibodies.

CDCP1 polypeptides can be used for the identification of agents for use in the methods of treatment and/or prophylaxis according to the invention.

A further aspect of the invention provides methods of screening for anti-ovarian cancer agents that interact with a CDCP1 polypeptide comprising:
  (a) contacting said polypeptide with a candidate agent; and
  (b) determining whether or not the candidate agent interacts with said polypeptide.

Preferably, the determination of an interaction between the candidate agent and CDCP1 polypeptide comprises quantitatively detecting binding of the candidate agent and said polypeptide.

Further provided is a method of screening for anti-ovarian cancer agents that modulate the expression or activity of a CDCP1 polypeptide comprising:
  (i) comparing the expression or activity of said polypeptide in the presence of a candidate agent with the expression or activity of said polypeptide in the absence of the candidate agent or in the presence of a control agent; and
  (ii) determining whether the candidate agent causes the expression or activity of said polypeptide to change.

Preferably, the expression and/or activity of a CDCP1 polypeptide is compared with a predetermined reference range or control.

More preferably the method further comprises selecting an agent, which interacts with a CDCP1 polypeptide or is capable of modulating the interaction, expression or activity of a CDCP1 polypeptide, for further testing for use in the treatment and/or prophylaxis of ovarian cancer. It will be apparent to one skilled in the art that the above screening methods are also appropriate for screening for anti-ovarian cancer agents which interact with or modulate the expression or activity of a CDCP1 nucleic acid molecule.

The invention also provides assays for use in drug discovery in order to identify or verify the efficacy of agents for treatment and/or prophylaxis of ovarian cancer. Agents identified using these methods can be used as lead agents for drug discovery, or used therapeutically. Expression of a CDCP1 polypeptide can be assayed by, for example, immunoassays, gel electrophoresis followed by visualisation, detection of mRNA or CDCP1 polypeptide activity or any other method taught herein or known to those skilled in the art. Such assays can be used to screen candidate agents, in clinical monitoring or in drug development.

Agents can be selected from a wide variety of candidate agents. Examples of candidate agents include but are not limited to, nucleic acids (e.g. DNA and RNA), carbohydrates, lipids, proteins, polypeptides, peptides, peptidomimetics, small molecules and other drugs. Agents can be obtained using any of the numerous approaches in combinatorial library methods known in the art, including: biological libraries; spatially addressable parallel solid phase or solution phase libraries; synthetic library methods requiring deconvolution; the "one-bead one-compound" library method; and synthetic library methods using affinity chromatography selection. The biological library approach is suited to peptide libraries, while the other four approaches are applicable to peptide, non-peptide oligomer or small molecule libraries of compounds (Lam, 1997, *Anticancer Drug Des.* 12:145; U.S. Pat. No. 5,738,996; and U.S. Pat. No. 5,807,683).

Examples of suitable methods based on the present description for the synthesis of molecular libraries can be found in the art, for example in: DeWitt et al., 1993, *Proc. Natl. Acad. Sci. USA* 90:6909; Erb et al., 1994, *Proc. Natl. Acad. Sci. USA* 91:11422; Zuckermann et al., 1994, *J. Med. Chem.* 37:2678; Cho et al., 1993, *Science* 261:1303; Carrell et al., 1994, Angew. *Chem. Int. Ed. Engl.* 33:2059; Carell et al., 1994, Angew. *Chem. Int. Ed. Engl.* 33:2061; and Gallop et al., 1994, *J. Med. Chem.* 37:1233.

Libraries of compounds may be presented, for example, in solution (e.g. Houghten, 1992, *Bio/Techniques* 13:412-421), or on beads (Lam, 1991, *Nature* 354:82-84), chips (Fodor, 1993, *Nature* 364:555-556), bacteria (U.S. Pat. No. 5,223,409), spores (U.S. Pat. Nos. 5,571,698; 5,403,484; and 5,223,409), plasmids (Cull et al., 1992, *Proc. Natl. Acad. Sci. USA* 89:1865-1869) or phage (Scott, et al., 1990, *Science* 249:386-390; Devlin, 1990, *Science* 249:404-406; Cwirla et al., 1990, *Proc. Natl. Acad. Sci. USA* 87:6378-6382; and Felici, 1991, *J. Mol. Biol.* 222:301-310).

In one embodiment, agents that interact with (e.g. bind to) a CDCP1 polypeptide are identified in a cell-based assay where a population of cells expressing a CDCP1 polypeptide is contacted with a candidate agent and the ability of the candidate agent to interact with the polypeptide is determined. Preferably, the ability of a candidate agent to interact with a CDCP1 polypeptide is compared to a reference range or control. In another embodiment, a first and second population of cells expressing a CDCP1 polypeptide are contacted with a candidate agent or a control agent and the ability of the candidate agent to interact with the polypeptide is determined by comparing the difference in interaction between the candidate agent and control agent. If desired, this type of assay may be used to screen a plurality (e.g. a library) of candidate agents using a plurality of cell populations expressing a CDCP1 polypeptide. If desired, this assay may be used to screen a plurality (e.g. a library) of candidate agents. The cell, for example, can be of prokaryotic origin (e.g. *E. coli*) or eukaryotic origin (e.g. yeast or mammalian). Further, the cells can express the CDCP1 polypeptide endogenously or be genetically engineered to express the polypeptide. In some embodiments, a CDCP1 polypeptide or the candidate agent is labelled, for example with a radioactive label (such as $^{32}P$, $^{35}S$ or $^{125}I$) or a fluorescent label (such as fluorescein isothiocyanate, rhodamine, phycoerythrin, phycocyanin, allophycocyanin, o-phthaldehyde or fluorescamine) to enable detection of an interaction between a polypeptide and a candidate agent.

In another embodiment, agents that interact with (e.g. bind to) a CDCP1 polypeptide are identified in a cell-free assay system where a sample expressing a CDCP1 polypeptide is contacted with a candidate agent and the ability of the candidate agent to interact with the polypeptide is determined. Preferably, the ability of a candidate agent to interact with a CDCP1 polypeptide is compared to a reference range or control. In a preferred embodiment, a first and second sample comprising native or recombinant CDCP1 polypeptide are contacted with a candidate agent or a control agent and the ability of the candidate agent to interact with the polypeptide is determined by comparing the difference in interaction between the candidate agent and control agent. If desired, this assay may be used to screen a plurality (e.g. a library) of candidate agents using a plurality of CDCP1 polypeptide samples. Preferably, the polypeptide is first immobilized, by, for example, contacting the polypeptide with an immobilized antibody which specifically recognizes and binds it, or by contacting a purified preparation of polypeptide with a surface designed to bind proteins. The polypeptide may be partially or completely purified (e.g. partially or completely free of other polypeptides) or part of a cell lysate. Further, the polypeptide may be a fusion protein comprising the CDCP1 polypeptide or a biologically active portion thereof and a domain such as glutathionine-S-transferase. Alternatively, the polypeptide can be biotinylated using techniques well known to those of skill in the art (e.g. biotinylation kit, Pierce Chemicals; Rockford, Ill.). The ability of the candidate agent to interact with the polypeptide can be duplicated by methods known to those of skill in the art.

In one embodiment, a CDCP1 polypeptide is used as a "bait protein" in a two-hybrid assay or three hybrid assay to identify other proteins that bind to or interact with the CDCP1 polypeptide (see e.g. U.S. Pat. No. 5,283,317; Zervos et al., 1993, *Cell* 72:223-232; Madura et al. 1993, *J. Biol. Chem.* 268:12046-12054; Bartel et al., 1993, *Bio/Techniques* 14:920-924; Iwabuchi et al., 1993, *Oncogene* 8:1693-1696; and WO 94/10300). As those skilled in the art will appreciate, such binding proteins are also likely to be involved in the propagation of signals by a CDCP1 polypeptide. For example, they may be upstream or downstream elements of a signalling pathway involving a CDCP1 polypeptide. Alternatively, polypeptides that interact with a CDCP1 polypeptide can be identified by isolating a protein complex comprising a CDCP1 polypeptide (said polypeptide may interact directly or indirectly with one or more other polypeptides) and identifying the associated proteins using methods known in the art such as mass spectrometry or Western blotting (for examples see Blackstock, et al., 1999, *Trends in Biotechnology*, 17: 121-127; Rigaut, 1999, *Nature Biotechnology*, 17: 1030-1032; Husi, 2000, *Nature Neurosci.* 3:661-669; Ho, Y. et al., 2002, *Nature*, 415:180-183; Gavin, et al., 2002, *Nature*, 415: 141-147).

In all cases, the ability of the candidate agent to interact directly or indirectly with the CDCP1 polypeptide can be determined by methods known to those of skill in the art. For example but without limitation, the interaction between a candidate agent and a CDCP1 polypeptide can be determined by flow cytometry, a scintillation assay, an activity assay, mass spectrometry, microscopy, immunoprecipitation or western blot analysis.

In yet another embodiment, agents that competitively interact with (i.e. competitively binding to) a CDCP1 polypeptide are identified in a competitive binding assay and the ability of the candidate agent to interact with the CDCP1 polypeptide is determined. Preferably, the ability of a candidate agent to interact with a CDCP1 polypeptide is compared to a reference range or control. In a preferred embodiment, a first and second population of cells expressing both a CDCP1 polypeptide and a protein which is known to interact with the CDCP1 polypeptide are contacted with a candidate agent or a control agent. The ability of the candidate agent to competitively interact with the CDCP1 polypeptide is then determined by comparing the interaction in the first and second population of cells. In another embodiment, an alternative second population or a further population of cells may be contacted with an agent which is known to competitively interact with a CDCP1 polypeptide. Alternatively, agents that competitively interact with a CDCP1 polypeptide are identified in a cell-free assay system by contacting a first and second sample comprising a CDCP1 polypeptide and a protein known to interact with the CDCP1 polypeptide with a candidate agent or a control agent. The ability of the candidate agent to competitively interact with the CDCP1 polypeptide is then determined by comparing the interaction in the first and second sample. In another embodiment, an alternative second sample or a further sample comprising a CDCP1 polypeptide may be contacted with an agent which is known to competitively interact with a CDCP1 polypeptide. In any case, the CDCP1 polypeptide and known interacting protein may be expressed naturally or may be recombinantly expressed; the candidate agent may be added exogenously, or be expressed naturally or recombinantly.

In another embodiment, agents that modulate the interaction between a CDCP1 polypeptide and another agent, for example but without limitation a protein, may be identified in a cell-based assay by contacting cells expressing a CDCP1 polypeptide in the presence of a known interacting agent and a candidate modulating agent and selecting the candidate agent which modulates the interaction. Alternatively, agents that modulate an interaction between a CDCP1 polypeptide and another agent, for example but without limitation a protein, may be identified in a cell-free assay system by contacting the polypeptide with an agent known to interact with the polypeptide in the presence of a candidate agent. A modulating agent can act as an antibody, a cofactor, an inhibitor, an activator or have an antagonistic or agonistic effect on the interaction between a CDCP1 polypeptide and a known agent. As stated above the ability of the known agent to interact with a CDCP1 polypeptide can be determined by methods known in the art. These assays, whether cell-based or cell-free, can be used to screen a plurality (e.g. a library) of candidate agents.

In another embodiment, a cell-based assay system is used to identify agents capable of modulating (i.e. stimulating or inhibiting) the activity of a CDCP1 polypeptide. Accordingly, the activity of a CDCP1 polypeptide is measured in a population of cells that naturally or recombinantly express a CDCP1 polypeptide, in the presence of a candidate agent. Preferably, the activity of a CDCP1 polypeptide is compared to a reference range or control. In a preferred embodiment, the activity of a CDCP1 polypeptide is measured in a first and second population of cells that naturally or recombinantly express a CDCP1 polypeptide, in the presence of agent or absence of a candidate agent (e.g. in the presence of a control agent) and the activity of the CDCP1 polypeptide is compared. The candidate agent can then be identified as a modulator of the activity of a CDCP1 polypeptide based on this comparison. Alternatively, the activity of a CDCP1 polypeptide can be measured in a cell-free assay system where the CDCP1 polypeptide is either natural or recombinant. Preferably, the activity of a CDCP1 polypeptide is compared to a reference range or control. In a preferred embodiment, the activity of a CDCP1 polypeptide is measured in a first and second sample in the presence or absence of a candidate agent and the activity of the CDCP1 polypeptide is compared. The candidate agent can then be identified as a modulator of the activity of a CDCP1 polypeptide based on this comparison.

The activity of a CDCP1 polypeptide can be assessed by detecting its effect on a downstream effector, for example but without limitation, the level or activity of a second messenger (e.g. cAMP, intracellular $Ca^{2+}$, diacylglycerol, $IP_3$, etc.), detecting catalytic or enzymatic activity, detecting the induction of a reporter gene (e.g. luciferase) or detecting a cellular response, for example, proliferation, differentiation or transformation where appropriate as known by those skilled in the art (for activity measurement techniques see, e.g. U.S. Pat. No. 5,401,639). The candidate agent can then be identified as a modulator of the activity of a CDCP1 polypeptide by comparing the effects of the candidate agent to the control agent. Suitable control agents include PBS or normal saline.

In another embodiment, agents such as an enzyme, or a biologically active portion thereof, which is responsible for the production or degradation of a CDCP1 polypeptide or is responsible for the post-translational modification of a CDCP1 polypeptide can be identified. In a primary screen, substantially pure, native or recombinantly expressed CDCP1 polypeptides, nucleic acids or cellular extract or other sample comprising native or recombinantly expressed CDCP1 polypeptides or nucleic acids are contacted with a plurality of candidate agents (for example but without limitation, a plurality of agents presented as a library) that may be responsible for the processing of a CDCP1 polypeptide or nucleic acid, in order to identify such agents. The ability of the candidate agent to modulate the production, degradation or post-translational modification of a CDCP1 polypeptide or nucleic acid can be determined by methods known to those of skill in the art, including without limitation, flow cytometry, radiolabelling, a kinase assay, a phosphatase assay, immunoprecipitation and Western blot analysis, or Northern blot analysis.

In yet another embodiment, cells expressing a CDCP1 polypeptide are contacted with a plurality of candidate agents. The ability of such an agent to modulate the production, degradation or post-translational modification of a CDCP1 polypeptide can be determined by methods known to those of skill in the art, as described above.

In one embodiment, agents that modulate the expression of a CDCP1 polypeptide (e.g. down-regulate) are identified in a cell-based assay system. Accordingly, a population of cells expressing a CDCP1 polypeptide or nucleic acid are contacted with a candidate agent and the ability of the candidate agent to alter expression of the CDCP1 polypeptide or nucleic acid is determined by comparison to a reference range or control. In another embodiment, a first and second population of cells expressing a CDCP1 polypeptide are contacted with a candidate agent or a control agent and the ability of the candidate agent to alter the expression of the CDCP1 polypeptide or nucleic acid is determined by comparing the difference in the level of expression of the CDCP1 polypeptide or nucleic acid between the first and second populations of cells. In a further embodiment, the expression of the CDCP1 polypeptide or nucleic acid in the first population may be further compared to a reference range or control. If desired, this assay may be used to screen a plurality (e.g. a library) of candidate agents. The cell, for example, can be of prokaryotic origin (e.g. *E. coli*) or eukaryotic origin (e.g. yeast or mammalian). Further, the cells can express a CDCP1 polypeptide or nucleic acid endogenously or be genetically engineered to express a CDCP1 polypeptide or nucleic acid. The ability of the candidate agents to alter the expression of a CDCP1 polypeptide or nucleic acid can be determined by methods known to those of skill in the art, for example and without limitation, by flow cytometry, radiolabelling, a scintillation assay, immunoprecipitation, Western blot analysis or Northern blot analysis.

In another embodiment, agents that modulate the expression of a CDCP1 polypeptide or nucleic acid are identified in an animal model. Examples of suitable animals include, but are not limited to, mice, rats, rabbits, monkeys, guinea pigs, dogs and cats. Preferably, the animal used represents a model of ovarian cancer. Accordingly, a first and second group of mammals are administered with a candidate agent or a control agent and the ability of the candidate agent to modulate the expression of the CDCP1 polypeptide or nucleic acid is determined by comparing the difference in the level of expression between the first and second group of mammals. Where desired, the expression levels of the CDCP1 polypeptides or nucleic acid in the first and second groups of mammals can be compared to the level of a CDCP1 polypeptide or nucleic acid in a control group of mammals. The candidate agent or a control agent can be administered by means known in the art (e.g. orally, rectally or parenterally such as intraperitoneally or intravenously). Changes in the expression of a polypeptide or nucleic acid can be assessed by the methods outlined above. In a particular embodiment, a therapeutically effective amount of an agent can be determined by monitoring an amelioration or improvement in disease symptoms, to delay onset or slow progression of the disease, for example but without limitation, a reduction in tumour size. Techniques known to physicians familiar with ovarian cancer can be used to determine whether a candidate agent has altered one or more symptoms associated with the disease.

One skilled in the art will also appreciate that a CDCP1 polypeptide may also be used in a method for the structure-based design of an agent, in particular a small molecule which acts to modulate (e.g. stimulate or inhibit) the activity of said polypeptide, said method comprising:
1) determining the three-dimensional structure of said polypeptide;
2) deducing the three-dimensional structure within the polypeptide of the likely reactive or binding site(s) of the agent;
3) synthesising candidate agents that are predicted to react or bind to the deduced reactive or binding site; and
4) testing whether the candidate agent is able to modulate the activity of said polypeptide.

It will be appreciated that the method described above is likely to be an iterative process.

As discussed herein, agents which interact with a CDCP1 polypeptide find use in the treatment and/or prophylaxis of ovarian cancer. For such use the agents will generally be administered in the form of a pharmaceutical composition.

Thus, according to the invention there is provided a pharmaceutical composition comprising an agent which interacts with a CDCP1 polypeptide and a pharmaceutically acceptable diluent, excipient and/or carrier. Pharmaceutical compositions may also find use as a vaccine and may comprise additional components acceptable for vaccine use and may additionally comprise one or more suitable adjuvants as known to the skilled person.

Hereinafter, the agents of use in the invention, CDCP1 polypeptides and CDCP1 nucleic acids of use in treatment and/or prophylaxis are referred to as 'active agents'. When a reference is made herein to a method of treating or preventing a disease or condition using a particular active agent or combination of agents, it is to be understood that such a reference is intended to include the use of that active agent or combination of agents in the preparation of a medicament for the treatment and/or prophylaxis of the disease or condition.

The composition will usually be supplied as part of a sterile, pharmaceutical composition that will normally include a pharmaceutically acceptable carrier. This composition may be in any suitable form (depending upon the desired method of administering it to a patient).

Active agents of the invention may be administered to a subject by any of the routes conventionally used for drug administration, for example they may be administered parenterally, orally, topically (including buccal, sublingual or transdermal) or by inhalation. The most suitable route for administration in any given case will depend on the particular active agent, the subject, and the nature and severity of the disease and the physical condition of the subject.

The active agents may be administered in combination, e.g. simultaneously, sequentially or separately, with one or more other therapeutically active, e.g. anti-tumour, compounds.

Pharmaceutical compositions may be conveniently presented in unit dose forms containing a predetermined amount of an active agent of the invention per dose. Such a unit may contain for example but without limitation, 750 mg/kg to 0.1 mg/kg depending on the condition being treated, the route of administration and the age, weight and condition of the subject.

Pharmaceutically acceptable carriers for use in the invention may take a wide variety of forms depending, e.g. on the route of administration.

Compositions for oral administration may be liquid or solid. Oral liquid preparations may be in the form of, for example, aqueous or oily suspensions, solutions, emulsions, syrups or elixirs, or may be presented as a dry product for reconstitution with water or other suitable vehicle before use. Oral liquid preparations may contain suspending agents as known in the art.

In the case of oral solid preparations such as powders, capsules and tablets, carriers such as starches, sugars, microcrystalline cellulose, diluents, granulating agents, lubricants, binders, disintegrating agents, and the like may be included. Because of their ease of administration, tablets and capsules represent the most advantageous oral dosage unit form in which case solid pharmaceutical carriers are generally employed. In addition to the common dosage forms set out above, active agents of the invention may also be administered by controlled release means and/or delivery devices. Tablets and capsules may comprise conventional carriers or excipients such as binding agents for example, syrup, acacia, gelatin, sorbitol, tragacanth, or polyvinylpyrrolidone; fillers, for example lactose, sugar, maize-starch, calcium phosphate, sorbitol or glycine; tableting lubricants, for example magnesium stearate, talc, polyethylene glycol or silica; disintegrants, for example potato starch; or acceptable wetting agents such as sodium lauryl sulphate. The tablets may be coated by standard aqueous or non-aqueous techniques according to methods well known in normal pharmaceutical practice.

Pharmaceutical compositions of the present invention suitable for oral administration may be presented as discrete units such as capsules, cachets or tablets, each containing a predetermined amount of the active agent, as a powder or granules, or as a solution or a suspension in an aqueous liquid, a non-aqueous liquid, an oil-in-water emulsion or a water-in-oil liquid emulsion. Such compositions may be prepared by any of the methods of pharmacy but all methods include the step of bringing into association the active agent with the carrier, which constitutes one or more necessary ingredients. In general, the compositions are prepared by uniformly and intimately admixing the active agent with liquid carriers or finely divided solid carriers or both, and then, if necessary, shaping the product into the desired presentation. For example, a tablet may be prepared by compression or moulding, optionally with one or more accessory ingredients.

Pharmaceutical compositions suitable for parenteral administration may be prepared as solutions or suspensions of the active agents of the invention in water suitably mixed with a surfactant such as hydroxypropylcellulose. Dispersions can also be prepared in glycerol, liquid polyethylene glycols, and mixtures thereof in oils. Under ordinary conditions of storage and use, these preparations contain a preservative to prevent the growth of microorganisms.

The pharmaceutical forms suitable for injectable use include aqueous or non-aqueous sterile injection solutions which may contain anti-oxidants, buffers, bacteriostats and solutes which render the composition isotonic with the blood of the intended recipient, and aqueous and non-aqueous sterile suspensions which may include suspending agents and thickening agents. Extemporaneous injection solutions, dispersions and suspensions may be prepared from sterile powders, granules and tablets.

Pharmaceutical compositions can be administered with medical devices known in the art. For example, in a preferred embodiment, a pharmaceutical composition of the invention can be administered with a needleless hypodermic injection device, such as the devices disclosed in U.S. Pat. Nos. 5,399, 163; 5,383,851; 5,312,335; 5,064,413; 4,941,880; 4,790,824; or 4,596,556. Examples of well-known implants and modules useful in the present invention include: U.S. Pat. No. 4,487, 603, which discloses an implantable micro-infusion pump for dispensing medication at a controlled rate; U.S. Pat. No. 4,486,194, which discloses a therapeutic device for administering medicaments through the skin; U.S. Pat. No. 4,447, 233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments; and U.S. Pat. No. 4,475,196, which discloses an osmotic drug delivery system. Many other such implants, delivery systems, and modules are known to those skilled in the art.

In certain embodiments, the pharmaceutical compositions of the invention can be formulated to ensure proper distribution in vivo. For example, the blood-brain barrier excludes many highly hydrophilic compounds and it may be preferable to deliver pharmaceutical compositions in liposomes. Thus, in one embodiment of the invention, the active agents of the invention are formulated in liposomes; in a more preferred embodiment, the liposomes include a targeting moiety. In a most preferred embodiment, the therapeutic compounds in the liposomes are delivered by bolus injection to a site proximal to the tumour. For methods of manufacturing liposomes, see, e.g. U.S. Pat. Nos. 4,522,811; 5,374,548; and 5,399,331. The liposomes may comprise one or more moieties which are selectively transported into specific cells or organs, thus enhancing targeted drug delivery (see, e.g. Ranade, 1989, *J. Clin. Pharmacol.* 29:685). Exemplary targeting moieties include folate or biotin (see, e.g. U.S. Pat. No. 5,416,016.); mannosides (Umezawa et al., 1988, *Biochem. Biophys. Res. Commun.* 153:1038); antibodies (Bloeman, et al., 1995, *FEBS Lett.* 357:140; M. Owais et al., 1995, *Antimicrob. Agents Chemother.* 39:180); surfactant protein A receptor (Briscoe et al., 1995, *Am. J. Physiol.* 1233:134), different species of which may comprise the formulations of the inventions, as well as components of the invented molecules; p120 (Schreier et al., 1994, *J. Biol. Chem.* 269:9090); see also Keinanen, et al., 1994, *FEBS Lett.* 346:123; Killion, et al., 1994, *Immunomethods* 4:273. The compositions may be presented in unit-dose or multi-dose containers, for example in sealed ampoules and vials and to enhance stability, may be stored in a freeze-dried (lyophilized) condition requiring only the addition of the sterile liquid carrier, for example water for injections, immediately prior to use. The sterile liquid carrier may be supplied in a separate vial or ampoule and can be a solvent or dispersion medium containing, for example, water, ethanol, polyol (e.g. glycerol, propylene glycol and liquid polyethylene glycol), suitable mixtures thereof, and vegetable oils. Advantageously, agents such as a local anaesthetic, preservative and buffering agents can be included the sterile liquid carrier.

Pharmaceutical compositions adapted for topical administration may be formulated as ointments, creams, suspensions, lotions, powders, solutions, pastes, gels, impregnated dressings, sprays, aerosols or oils, transdermal devices, dusting powders, and the like. These compositions may be prepared via conventional methods containing the active agent. Thus, they may also comprise compatible conventional carriers and additives, such as preservatives, solvents to assist drug penetration, emollients in creams or ointments and ethanol or oleyl alcohol for lotions. Such carriers may be present as from about 1% up to about 98% of the composition. More usually they will form up to about 80% of the composition. As an illustration only, a cream or ointment is prepared by mixing sufficient quantities of hydrophilic material and water, containing from about 5-10% by weight of the compound, in sufficient quantities to produce a cream or ointment having the desired consistency.

Pharmaceutical compositions adapted for transdermal administration may be presented as discrete patches intended to remain in intimate contact with the epidermis of the recipient for a prolonged period of time. For example, the active agent may be delivered from the patch by iontophoresis.

For applications to external tissues, for example the mouth and skin, the compositions are preferably applied as a topical ointment or cream. When formulated in an ointment, the active agent may be employed with either a paraffinic or a water-miscible ointment base. Alternatively, the active agent may be formulated in a cream with an oil-in-water cream base or a water-in-oil base.

Pharmaceutical compositions adapted for topical administration in the mouth include lozenges, pastilles and mouth washes.

Pharmaceutical compositions adapted for topical administration to the eye include eye drops wherein the active agent is dissolved or suspended in a suitable carrier, especially an aqueous solvent. They also include topical ointments or creams as above.

Pharmaceutical compositions suitable for rectal administration wherein the carrier is a solid are most preferably presented as unit dose suppositories. Suitable carriers include cocoa butter or other glyceride or materials commonly used in the art, and the suppositories may be conveniently formed by admixture of the combination with the softened or melted carrier(s) followed by chilling and shaping moulds. They may also be administered as enemas.

Pharmaceutical compositions adapted for vaginal administration may be presented as pessaries, tampons, creams, gels, pastes, foams or spray compositions. These may comprise emollients or bases as commonly used in the art.

The dosage to be administered of an active agent will vary according to the particular active agent, the subject, and the nature and severity of the disease and the physical condition of the subject, and the selected route of administration; the appropriate dosage can be readily determined by a person skilled in the art. For the treatment and/or prophylaxis of ovarian cancer in humans and animals pharmaceutical compositions comprising antibodies can be administered to patients (e.g., human subjects) at therapeutically or prophylactically effective dosages (e.g. dosages which result in tumour growth inhibition and/or tumour cell migration inhibition) using any suitable route of administration, such as injection and other routes of administration known in the art for antibody-based clinical products.

The compositions may contain from 0.1% by weight, preferably from 10-60%, or more, by weight, of the active agent of the invention, depending on the method of administration.

It will be recognized by one of skill in the art that the optimal quantity and spacing of individual dosages of an active agent of the invention will be determined by the nature and extent of the condition being treated, the form, route and site of administration, and the age and condition of the particular subject being treated, and that a physician will ultimately determine appropriate dosages to be used. This dosage may be repeated as often as appropriate. If side effects develop the amount and/or frequency of the dosage can be altered or reduced, in accordance with normal clinical practice.

CDCP1 polypeptides may also be of use in the treatment and/or prophylaxis of ovarian cancer. Accordingly, provided is a method for the treatment and/or prophylaxis of ovarian cancer comprising administering a therapeutically effective amount of a composition comprising a CDCP1 polypeptide, preferably as a vaccine. Also provided is the use of a CDCP1 polypeptide for the manufacture of a medicament for the treatment and/or prophylaxis of ovarian cancer. Where they are provided for use with the methods of the invention CDCP1 are preferably provided in isolated form. More preferably the CDCP1 polypeptides have been purified to at least some extent. CDCP1 polypeptides can also be produced using recombinant methods, synthetically produced or produced by a combination of these methods. CDCP1 polypeptides may be provided in substantially pure form, that is to say free, to a substantial extent, from other proteins.

Recombinant CDCP1 polypeptides may be prepared by processes well known in the art from genetically engineered host cells comprising expression systems. Accordingly, the present invention also relates to expression systems which comprise a CDCP1 polypeptide or CDCP1 nucleic acid, to host cells which are genetically engineered with such expression systems and to the production of CDCP1 polypeptides by recombinant techniques. Cell-free translation systems can also be employed to produce recombinant polypeptides (e.g. rabbit reticulocyte lysate, wheat germ lysate, SP6/T7 in vitro T&T and RTS100 *E. Coli* HY transcription and translation kits from Roche Diagnostics Ltd., Lewes, UK and the TNT Quick coupled Transcription/Translation System from Promega UK, Southampton, UK.

For recombinant CDCP1 polypeptide production, host cells can be genetically engineered to incorporate expression systems or portions thereof for CDCP1 nucleic acids. Such incorporation can be performed using methods well known in the art, such as, calcium phosphate transfection, DEAD-dextran mediated transfection, transvection, microinjection, cationic lipid-mediated transfection, electroporation, transduction, scrape loading, ballistic introduction or infection (see e.g. Davis et al., *Basic Methods in Molecular Biology*, 1986 and Sambrook et al., *Molecular Cloning: A Laboratory Manual*, 2$^{nd}$ Ed., Cold Spring Harbour laboratory Press, Cold Spring Harbour, N.Y., 1989).

Representative examples of host cells include bacterial cells e.g. *E. Coli, Streptococci, Staphylococci, Streptomyces* and *Bacillus subtilis* cells; fungal cells, such as yeast cells and *Aspergillus* cells; insect cells such as *Drosophila* S2 and *Spodoptera* Sf9 cells; animal cells such as CHO, COS, HeLa, C127, 3T3, HEK 293, BHK and Bowes melanoma cells; and plant cells.

A wide variety of expression systems can be used, such as and without limitation, chromosomal, episomal and virus-derived systems, e.g. vectors derived from bacterial plasmids, from bacteriophage, from transposons, from yeast episomes, from insertion elements, from yeast chromosomal elements, from viruses such as baculoviruses, papova viruses such as SV40, vaccinia viruses, adenoviruses, fowl pox viruses, pseudorabies viruses and retroviruses, and vectors derived from combinations thereof, such as those derived from plasmid and bacteriophage genetic elements, such as cosmids and phagemids. The expression systems may contain control regions that regulate as well as engender expression. Generally, any system or vector which is able to maintain, propagate or express a nucleic acid to produce a polypeptide in a host may be used. The appropriate nucleic acid sequence may be inserted into an expression system by any variety of well-known and routine techniques, such as those set forth in Sambrook et al., supra. Appropriate secretion signals may be incorporated into the CDCP1 polypeptide to allow secretion of the translated protein into the lumen of the endoplasmic reticulum, the periplasmic space or the extracellular environment. These signals may be endogenous to the CDCP1 polypeptide or they may be heterologous signals.

If a CDCP1 polypeptide is to be expressed for use in cell-based screening assays, it is preferred that the polypeptide be produced at the cell surface. In this event, the cells may be harvested prior to use in the screening assay. If the CDCP1 polypeptide is secreted into the medium, the medium can be recovered in order to isolate said polypeptide. If produced intracellularly, the cells must first be lysed before the CDCP1 polypeptide is recovered.

CDCP1 polypeptides can be recovered and purified from recombinant cell cultures or from other biological sources by well-known methods including, ammonium sulphate or ethanol precipitation, acid extraction, anion or cation exchange chromatography, phosphocellulose chromatography, affinity chromatography, hydrophobic interaction chromatography, hydroxylapatite chromatography, molecular sieving chromatography, centrifugation methods, electrophoresis methods and lectin chromatography. In one embodiment, a combination of these methods is used. In another embodiment, high performance liquid chromatography is used. In a further embodiment, an antibody which specifically binds to a CDCP1 polypeptide can be used to deplete a sample comprising a CDCP1 polypeptide of said polypeptide or to purify said polypeptide. Techniques well-known in the art, may be used for refolding to regenerate native or active conformations of the CDCP1 polypeptides when the polypeptides have been denatured during isolation and or purification. In the context of the present invention, CDCP1 polypeptides can be obtained from a biological sample from any source, such as and without limitation, an ovarian tissue sample or other tissue sample.

CDCP1 polypeptides may be in the form of a 'mature' protein or may be part of a larger protein such as a fusion protein. It is often advantageous to include an additional amino acid sequence which contains secretory or leader sequences, a pre-, pro- or prepro-protein sequence, or a sequence which aids in purification such as an affinity tag, for example, but without limitation, multiple histidine residues, a FLAG tag, HA tag or myc tag. An additional sequence which may provide stability during recombinant production may also be used. Such sequences may be optionally removed as required by incorporating a cleavable sequence as an additional sequence or part thereof. Thus, a CDCP1 polypeptide may be fused to other moieties including other polypeptides. Such additional sequences and affinity tags are well known in the art.

Amino acid substitutions may be conservative or semi-conservative as known in the art and preferably do not significantly affect the desired activity of the polypeptide. Substitutions may be naturally occurring or may be introduced for example using mutagenesis (e.g. Hutchinson et al., 1978, *J. Biol. Chem.* 253:6551). Thus, the amino acids glycine, alanine, valine, leucine and isoleucine can often be substituted for one another (amino acids having aliphatic side chains). Of these possible substitutions, it is preferred that glycine and alanine are used to substitute for one another (since they have relatively short side chains) and that valine, leucine and isoleucine are used to substitute for one another (since they have larger aliphatic side chains which are hydrophobic). Other amino acids which can often be substituted for one another include but are not limited to:

phenylalanine, tyrosine and tryptophan (amino acids having aromatic side chains);

lysine, arginine and histidine (amino acids having basic side chains);

aspartate and glutamate (amino acids having acidic side chains);

asparagine and glutamine (amino acids having amide side chains);

cysteine and methionine (amino acids having sulphur-containing side chains); and aspartic acid and glutamic acid can substitute for phospho-serine and phospho-threonine, respectively (amino acids with acidic side chains).

In one particular embodiment, the substituted amino acid(s) do significantly affect the activity of the CDCP1 polypeptide and may be selected specifically to render dominant negative activity upon the peptide. In another embodiment, the substituted amino acid(s) may be selected specifically to render the polypeptide constitutively active.

Modifications include naturally occurring modifications such as and without limitation, post-translational modifications and also non-naturally occurring modifications such as may be introduced by mutagenesis.

Preferably a derivative of a CDCP1 polypeptide has at least 70% identity to the amino acid sequence shown in FIG. 1 (SEQ ID NO:1), more preferably it has at least 75%, at least 80%, at least 85%, at least 90%, at least 95% or at least 98% identity. Percentage identity is a well known concept in the art and can be calculated using, for example but without limitation, the BLASTT™ software available from NCBI (Altschul, et al., 1990, *J. Mol. Biol.* 215:403-410; Gish, et al., 1993, *Nature Genet.* 3:266-272. Madden, et al., 1996, *Meth. Enzymol.* 266:131-141; Altschul, et al., 1997, *Nucleic Acids Res.* 25:3389-3402; Zhang, et al., 1997, *Genome Res.* 7:649-656).

A fragment of a CDCP1 polypeptide may also be of use in the methods of the invention and includes a fragment of a polypeptide having the amino acid sequence of SEQ ID NO:1, which has at least 70% homology over the length of the fragment. Preferably, said fragments are at least 10 amino acids in length, preferably they are at least 20, at least 30, at least 50 or at least 100 amino acids in length. A fragment has at least 70% identity over its length to the amino acid sequence shown in FIG. 1 (SEQ ID NO: 1), more preferably it has at least 75%, at least 80%, at least 85%, at least 90%, at least 95% or at least 98% identity.

Where a CDCP1 polypeptide is the active agent of a pharmaceutical composition for use in the treatment and/or prophylaxis of ovarian cancer, preferably recombinant CDCP1 polypeptides are used. In a particular embodiment, a CDCP1 polypeptide fused to another polypeptide, such as the protein transduction domain of the HIV/Tat protein which facilitates the entry of the fusion protein into a cell (Asoh, et al., 2002, *Proc. Natl. Acad. Sci. USA*, 99:17107-17112), is provided for use in the manufacture of a medicament for the treatment and/or prophylaxis of ovarian cancer.

In another aspect, detection of a CDCP1 polypeptide in a subject with ovarian cancer may be used to identify in particular an appropriate patient population for treatment according to the methods of the invention.

Accordingly, the present invention provides a method of screening for and/or diagnosis or prognosis of ovarian cancer in a subject, and/or monitoring the effectiveness of ovarian cancer therapy, which comprises the step of detecting and/or quantifying in a biological sample obtained from said subject a CDCP1 polypeptide. The CDCP1 polypeptide for use in the method of screening and/or diagnosis preferably:

(a) comprises or consists of the amino acid sequence of SEQ ID NO:1;

(b) is a derivative having one or more amino acid substitutions, modifications, deletions or insertions relative to the amino acid sequence of SEQ ID NO:1 which retains the activity of CDCP1; or (c) is a fragment of a polypeptide having the amino acid sequence of SEQ ID NO: 1, which is at least ten amino acids long and has at least 70% homology over the length of the fragment.

In one aspect, the expression is compared to a previously determined reference range. Preferably, the step of detecting comprises:

(a) contacting the sample with a capture reagent that is specific for a polypeptide as defined in (a) to (c), above; and (b) detecting whether binding has occurred between the capture reagent and said polypeptide in the sample.

In another aspect, the captured polypeptide is detected using a directly or indirectly labelled detection reagent which may be immobilised on a solid phase.

A convenient means for detecting/quantifying a CDCP1 polypeptide involves the use of antibodies. A CDCP1 polypeptide can be used as an immunogen to raise antibodies which interact with (bind to or recognise) said polypeptide using methods known in the art as described above. Thus, in a further aspect, the present invention provides the use of an antibody that specifically binds to at least one CDCP1 polypeptide for screening for and/or diagnosis of ovarian cancer in a subject or for monitoring the efficacy of an anti-ovarian cancer therapy. In a particular embodiment, the methods of diagnosis using an anti-CDCP1 polypeptide antibody can be used to identify an appropriate patient population for treatment according to the methods of the invention.

CDCP1 antibodies can also be used, inter alia, for the diagnosis of ovarian cancer by detecting CDCP1 expression in a biological sample of human tissue and/or in subfractions thereof, for example but without limitation, membrane, cytosolic or nuclear subfractions.

In a further aspect, the method of detecting a CDCP1 polypeptide in a biological sample comprises detecting and/or quantitating the amount of the CDCP1 polypeptide in said sample using a directly or indirectly labelled detection reagent. A CDCP1 polypeptide can be detected by means of any immunoassay known in the art, including, without limitation, immunoprecipitation followed by sodium dodecyl sulfate polyacrylamide gel electrophoresis, 2 dimensional gel electrophoresis, competitive and non-competitive assay systems using techniques such as Western blots, radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays and protein A immunoassays.

Detection of the interaction of an antibody with an antigen can be facilitated by coupling the antibody to a detectable substance for example, but without limitation, an enzyme (such as horseradish peroxidase, alkaline phosphatase, beta-galactosidase, acetylcholinesterase), a prosthetic group (such as streptavidin, avidin, biotin), a fluorescent material (such as umbelliferone, fluorescein, fluorescein isothiocyanate, rhodamine, dichlorotriazinylamine fluorescein, dansyl chloride, phycoerythrin), a luminescent material (such as luminol), a bioluminescent material (such as luciferase, luciferin, aequorin), a radioactive nuclide (such as $^{125}$I, $^{131}$I, $^{111}$In, $^{99}$Tc) a positron emitting metal or a non-radioactive paramagnetic metal ion (see U.S. Pat. No. 4,741,900).

The invention also provides diagnostic kits, comprising a capture reagent (e.g. an antibody) against a CDCP1 polypeptide as defined above. In addition, such a kit may optionally comprise one or more of the following:
(1) instructions for using the capture reagent for screening, diagnosis, prognosis, therapeutic monitoring or any combination of these applications;
(2) a labelled binding partner to the capture reagent;
(3) a solid phase (such as a reagent strip) upon which the capture reagent is immobilised; and
(4) a label or insert indicating regulatory approval for screening, diagnostic, prognostic or therapeutic use or any combination thereof.

If no labelled binding partner to the capture reagent is provided, the anti-CDCP1 polypeptide capture reagent itself can be labelled with a detectable marker, e.g. a chemiluminescent, enzymatic, fluorescent, or radioactive moiety (see above).

It will also be apparent to one skilled in the art that detection and/or quantitation of a CDCP1 nucleic acid may be used in a method of screening for and/or diagnosis or prognosis of ovarian cancer in a subject, and/or monitoring the effectiveness of ovarian cancer therapy.

Unless the context indicates otherwise, CDCP1 nucleic acids include those nucleic acid molecules which may have one or more of the following characteristics and thus may:
d) comprise or consist of the DNA sequence of SEQ ID NO:2 or its RNA equivalent;
e) have a sequence which is complementary to the sequences of d);
f) have a sequence which codes for a CDCP1 polypeptide;
g) have a sequence which shows substantial identity with any of those of d), e) and f); or
h) is a fragment of d), e), f) or g), which is at least 10 nucleotides in length;
and may have one or more of the following characteristics:
1) they may be DNA or RNA;
2) they may be single or double stranded;
3) they may be in substantially pure form. Thus, they may be provided in a form which is substantially free from contaminating proteins and/or from other nucleic acids; and
4) they may be with introns or without introns (e.g. as cDNA).

Fragments of CDCP1 nucleic acids are preferably at least 20, at least 30, at least 50, at least 100 or at least 250 nucleotides in length.

The invention also provides the use of nucleic acids which are complementary to the CDCP1 nucleic acids described in (d)-(h) above, and can hybridise to said CDCP1 nucleic acids. Such nucleic acid molecules are referred to as "hybridising" nucleic acid molecules. For example, but without limitation, hybridising nucleic acid molecules can be useful as probes or primers. Hybridising nucleic acid molecules may have a high degree of sequence identity along its length with a nucleic acid molecule within the scope of (d)-(h) above (e.g. at least 50%, at least 75%, at least 80%, at least 85%, at least 90%, at least 95%, or at least 98% sequence identity). The use of hybridising nucleic acid molecules that can hybridise to any of the nucleic acid molecules discussed above, e.g. in hybridising assays, is also covered by the present invention.

Hybridisation assays can be used for screening, prognosis, diagnosis, or monitoring of therapy of ovarian cancer in a subject. Accordingly, such a hybridisation assay comprises:
i) contacting a biological sample, obtained from a subject, containing nucleic acid with a nucleic acid probe capable of hybridising to a CDCP1 nucleic acid molecule, under conditions such that hybridisation can occur; and
ii) detecting or measuring any resulting hybridisation.

Preferably, such hybridising molecules are at least 10 nucleotides in length and are preferably at least 25 or at least 50 nucleotides in length. More preferably, the hybridising nucleic acid molecules specifically hybridise to nucleic acids within the scope of any one of (d) to (h), above. Most preferably, the hybridisation occurs under stringent hybridisation conditions. One example of stringent hybridisation conditions is where attempted hybridisation is carried out at a temperature of from about 35° C. to about 65° C. using a salt solution which is about 0.9M. However, the skilled person will be able to vary such conditions as appropriate in order to take into account variables such as probe length, base composition, type of ions present, etc.

The invention also provides a diagnostic kit comprising a nucleic acid probe capable of hybridising to RNA encoding a CDCP1 polypeptide, suitable reagents and instructions for use.

In a further embodiment, a diagnostic kit is provided comprising in one or more containers a pair of primers that under appropriate reaction conditions can prime amplification of at least a portion of a CDCP1 nucleic acid molecule, such as by polymerase chain reaction (see e.g. Innis et al., 1990, *PCR Protocols*, Academic Press, Inc., San Diego, Calif.), ligase chain reaction (see EP 320,308) use of Qβ replicase, cyclic probe reaction, or other methods known in the art. Typically, primers are at least eight nucleotides long and will preferably be at least ten to twenty-five nucleotides long and more preferably fifteen to twenty-five nucleotides long. In some cases, primers of at least thirty or at least thirty-five nucleotides in length may be used.

In yet another aspect, the present invention provides the use of at least one CDCP1 nucleic acid in the manufacture of a medicament for use in the treatment and/or prophylaxis of ovarian cancer.

In a specific embodiment, hybridising CDCP1 nucleic acid molecules are used as anti-sense molecules, to alter the expression of CDCP1 polypeptides by binding to complementary CDCP1 nucleic acids and can be used in the treatment and/or prophylaxis or prevention of ovarian cancer. An antisense nucleic acid includes a CDCP1 nucleic acid capable of hybridising by virtue of some sequence complementarity to a portion of an RNA (preferably mRNA) encoding a CDCP1 polypeptide. The antisense nucleic acid can be complementary to a coding and/or non-coding region of an mRNA encoding such a polypeptide. Most preferably, expression of a CDCP1 polypeptide is inhibited by use of antisense nucleic acids. Thus, the present invention provides the therapeutic or prophylactic use of nucleic acids comprising at least eight nucleotides that are antisense to a gene or cDNA encoding a CDCP1 polypeptide.

In another embodiment, symptoms of ovarian cancer may be ameliorated by decreasing the level or activity of a CDCP1 polypeptide by using gene sequences encoding a polypeptide as defined herein in conjunction with well-known gene "knock-out," ribozyme or triple helix methods to decrease gene expression of the polypeptide. In this approach, ribozyme or triple helix molecules are used to modulate the activity, expression or synthesis of the gene, and thus to ameliorate the symptoms of ovarian cancer. Such molecules may be designed to reduce or inhibit expression of a mutant or non-mutant target gene. Techniques for the production and use of such molecules are well known to those of skill in the art.

Endogenous CDCP1 polypeptide expression can also be reduced by inactivating or "knocking out" the gene encoding the polypeptide, or the promoter of such a gene, using targeted homologous recombination (e.g. see Smithies, et al., 1985, *Nature* 317:230-234; Thomas, et al., 1987, *Cell* 51:503-512; Thompson et al., 1989, *Cell* 5:313-321; and Zijlstra et al., 1989, *Nature* 342:435-438). For example, a mutant gene encoding a non-functional polypeptide (or a completely unrelated DNA sequence) flanked by DNA homologous to the endogenous CDCP1 gene (either the coding regions or regulatory regions of the gene encoding the polypeptide) can be used, with or without a selectable marker and/or a negative selectable marker, to transfect cells that express the target gene in vivo. Insertion of the DNA construct, via targeted homologous recombination, results in inactivation of the target gene.

In another embodiment, the nucleic acid is administered via gene therapy (see for example Hoshida, et al., 2002, *Pancreas*, 25:111-121; Ikuno, 2002, *Invest. Ophthalmol. Vis. Sci.* 2002 43:2406-2411; Bollard, 2002, *Blood* 99:3179-3187; Lee, 2001, *Mol. Med.* 7:773-782). Gene therapy refers to administration to a subject of an expressed or expressible CDCP1 nucleic acid. Any of the methods for gene therapy available in the art can be used according to the present invention.

Delivery of the therapeutic CDCP1 nucleic acid into a patient can be direct in vivo gene therapy (i.e. the patient is directly exposed to the nucleic acid or nucleic acid-containing vector) or indirect ex vivo gene therapy (i.e. cells are first transformed with the nucleic acid in vitro and then transplanted into the patient).

For example for in vivo gene therapy, an expression vector containing the CDCP1 nucleic acid is administered in such a manner that it becomes intracellular, i.e. by infection using a defective or attenuated retroviral or other viral vectors as described, for example, in U.S. Pat. No. 4,980,286 or by Robbins et al., 1998, *Pharmacol. Ther.* 80:35-47.

The various retroviral vectors that are known in the art are such as those described in Miller et al. (1993, *Meth. Enzymol.* 217:581-599) which have been modified to delete those retroviral sequences which are not required for packaging of the viral genome and subsequent integration into host cell DNA. Also adenoviral vectors can be used which are advantageous due to their ability to infect non-dividing cells and such high-capacity adenoviral vectors are described in Kochanek (1999, *Human Gene Therapy*, 10:2451-2459). Chimeric viral vectors that can be used are those described by Reynolds et al. (1999, *Molecular Medicine Today*, 1:25-31). Hybrid vectors can also be used and are described by Jacoby et al. (1997, *Gene Therapy*, 4:1282-1283).

Direct injection of naked DNA or through the use of microparticle bombardment (e.g. Gene Gun®; Biolistic, Dupont) or by coating it with lipids can also be used in gene therapy. Cell-surface receptors/transfecting compounds or through encapsulation in liposomes, microparticles or microcapsules or by administering the nucleic acid in linkage to a peptide which is known to enter the nucleus or by administering it in linkage to a ligand predisposed to receptor-mediated endocytosis (See Wu, et al., 1987, *J. Biol. Chem.*, 262:4429-4432) can be used to target cell types which specifically express the receptors of interest.

In another embodiment a nucleic acid ligand compound comprising a CDCP1 nucleic acid can be produced in which the ligand comprises a fusogenic viral peptide designed so as to disrupt endosomes, thus allowing the CDCP1 nucleic acid to avoid subsequent lysosomal degradation. The CDCP1 nucleic acid can be targeted in vivo for cell specific endocytosis and expression by targeting a specific receptor such as that described in WO92/06180, WO93/14188 and WO 93/20221. Alternatively the nucleic acid can be introduced intracellularly and incorporated within the host cell genome for expression by homologous recombination (See Zijlstra et al., 1989, *Nature*, 342:435-428).

In ex vivo gene therapy, a gene is transferred into cells in vitro using tissue culture and the cells are delivered to the patient by various methods such as injecting subcutaneously, application of the cells into a skin graft and the intravenous injection of recombinant blood cells such as haematopoietic stem or progenitor cells.

Cells into which a CDCP1 nucleic acid can be introduced for the purposes of gene therapy include, for example, epithelial cells, endothelial cells, keratinocytes, fibroblasts, muscle cells, hepatocytes and blood cells. The blood cells that can be used include, for example, T-lymphocytes, B-lymphocytes, monocytes, macrophages, neutrophils, eosinophils, megakaryotcytes, granulocytes, haematopoietic cells or progenitor cells, and the like.

In a one aspect, the pharmaceutical composition comprises a CDCP1 nucleic acid, said nucleic acid being part of an expression vector that expresses a CDCP1 polypeptide or chimeric protein thereof in a suitable host. In particular, such a nucleic acid has a promoter operably linked to the polypeptide coding region, said promoter being inducible or constitutive (and, optionally, tissue-specific). In another particular embodiment, a nucleic acid molecule is used in which the coding sequences and any other desired sequences are flanked by regions that promote homologous recombination at a desired site in the genome, thus providing for intrachromosomal expression of the nucleic acid (Koller, et al., 1989, *Proc. Natl. Acad. Sci. USA* 86:8932-8935; Zijlstra et al., 1989, *Nature* 342:435-438).

CDCP1 nucleic acids may be obtained using standard cloning and screening techniques, from a cDNA library derived from mRNA in human cells, using expressed sequence tag (EST) analysis (Adams, et al., 1991, *Science*, 252:1651-1656; Adams, et al., 1992, *Nature* 355:632-634; Adams, et al., 1995, *Nature*, 377:Suppl: 3-174). CDCP1 nucleic acids can also be obtained from natural sources such as genomic DNA libraries or can be synthesized using well known and commercially available techniques. The CDCP1 nucleic acids comprising coding sequence for CDCP1 polypeptides described above can be used for the recombinant production of said polypeptides. The CDCP1 nucleic acids may include the coding sequence for the mature polypeptide, by itself; or the coding sequence for the mature polypeptide in reading frame with other coding sequences, such as those encoding a leader or secretory sequence, a pre-, pro- or prepro-protein sequence, a cleavable sequence or other fusion peptide portions, such as an affinity tag or an additional sequence conferring stability during production of the polypeptide. Preferred affinity tags include multiple histidine residues (for example see Gentz et al., 1989, *Proc. Natl. Acad. Sci. USA* 86:821-824), a FLAG tag, HA tag or myc tag. The CDCP1 nucleic acids may also contain non-coding 5' and 3' sequences, such as transcribed, non-translated sequences, splicing and polyadenylation signals, ribosome binding sites and sequences that stabilize mRNA.

CDCP1 polypeptide derivatives above can be created by introducing one or more nucleotide substitutions, additions or deletions into the nucleotide sequence of a CDCP1 nucleic acid such that one or more amino acid substitutions, additions or deletions are introduced into the encoded protein. Standard techniques known to those of skill in the art can be used to introduce mutations, including, for example, site-directed mutagenesis and PCR-mediated mutagenesis. Preferably, conservative amino acid substitutions are made at one or more predicted non-essential amino acid residues.

A CDCP1 nucleic acid encoding a CDCP1 polypeptide, including homologues and orthologues from species other than human, may be obtained by a process which comprises the steps of screening an appropriate library under stringent hybridisation conditions with a labelled probe having the sequence of a CDCP1 nucleic acid as described in (d)-(h) above, and isolating full-length cDNA and genomic clones containing said nucleic acid sequence. Such hybridisation techniques are well-known in the art. One example of stringent hybridisation conditions is where attempted hybridisation is carried out at a temperature of from about 35° C. to about 65° C. using a salt solution of about 0.9M. However, the skilled person will be able to vary such conditions as appropriate in order to take into account variables such as probe length, base composition, type of ions present, etc. For a high degree of selectivity, relatively stringent conditions such as low salt or high temperature conditions, are used to form the duplexes. Highly stringent conditions include hybridisation to filter-bound DNA in 0.5M $NaHPO_4$, 7% sodium dodecyl sulphate (SDS), 1 mM EDTA at 65° C., and washing in 0.1×SSC/0.1% SDS at 68° C. (Ausubel et al., eds., 1989, *Current Protocols in Molecular Biology*, Vol. I, Green Publishing Associates, Inc., and John Wiley & Sons, Inc., New York, at p. 2.10.3). For some applications, less stringent conditions for duplex formation are required. Moderately stringent conditions include washing in 0.2×SSC/0.1% SDS at 42° C. (Ausubel et al., 1989, supra). Hybridisation conditions can also be rendered more stringent by the addition of increasing amounts of formamide, to destabilise the hybrid duplex. Thus, particular hybridisation conditions can be readily manipulated, and will generally be chosen as appropriate. In general, convenient hybridisation temperatures in the presence of 50% formamide are: 42° C. for a probe which is 95-100% identical to the fragment of a gene encoding a polypeptide as defined herein, 37° C. for 90-95% identity and 32° C. for 70-90% identity.

One skilled in the art will understand that, in many cases, an isolated cDNA sequence will be incomplete, in that the region coding for the polypeptide is cut short at the 5' end of the cDNA. This is a consequence of reverse transcriptase, an enzyme with inherently low processivity (a measure of the ability of the enzyme to remain attached to the template during the polymerization reaction), failing to complete a DNA copy of the mRNA template during $1^{st}$ strand cDNA synthesis.

Methods to obtain full length cDNAs or to extend short cDNAs are well known in the art, for example RACE (Rapid amplification of cDNA ends; e.g. Frohman et al., 1988, *Proc. Natl. Acad. Sci. USA* 85:8998-9002). Recent modifications of the technique, exemplified by the Marathon™ technology (Clontech Laboratories Inc.) have significantly simplified the search for longer cDNAs. This technology uses cDNAs prepared from mRNA extracted from a chosen tissue followed by the ligation of an adaptor sequence onto each end. PCR is then carried out to amplify the missing 5'-end of the cDNA using a combination of gene specific and adaptor specific oligonucleotide primers. The PCR reaction is then repeated using nested primers which have been designed to anneal with the amplified product, typically an adaptor specific primer that anneals further 3' in the adaptor sequence and a gene specific primer that anneals further 5' in the known gene sequence. The products of this reaction can then be analysed by DNA sequencing and a full length cDNA constructed either by joining the product directly to the existing cDNA to give a complete sequence, or carrying out a separate full length PCR using the new sequence information for the design of the 5' primer.

A further aspect of the invention relates to a vaccine composition of use in the treatment and/or prophylaxis of ovarian cancer. A CDCP1 polypeptide or nucleic acid as described above can be used in the production of vaccines for treatment and/or prophylaxis of ovarian cancer. Such material can be antigenic and/or immunogenic. Antigenic includes a protein or nucleic acid that is capable of being used to raise antibodies or indeed is capable of inducing an antibody response in a subject. Immunogenic material includes a protein or nucleic acid that is capable of eliciting an immune response in a subject. Thus, in the latter case, the protein or nucleic acid may be capable of not only generating an antibody response but, in addition, a non-antibody based immune responses, i.e. a cellular or humoral response. It is well known in the art that is possible to identify those regions of an antigenic or immunogenic polypeptide that are responsible for the antigenicity or immunogenicity of said polypeptide, i.e. an epitope or epitopes. Amino acid and peptide characteristics well known to the skilled person can be used to predict the antigenic index (a measure of the probability that a region is antigenic) of a CDCP1 polypeptide. For example, but without limitation, the 'Peptidestructure' program (Jameson, et al., 1988, *CABIOS*, 4(1):181) and a technique referred to as 'Threading' (Altuvia et al., 1995, *J. Mol. Biol.* 249:244) can be used. Thus, the CDCP1 polypeptides may include one or more such epitopes or be sufficiently similar to such regions so as to retain their antigenic/immunogenic properties.

Since a polypeptide or a nucleic acid may be broken down in the stomach, the vaccine composition is preferably administered parenterally (e.g. subcutaneous, intramuscular, intravenous or intradermal injection).

Accordingly, in further embodiments, the present invention provides:

a) the use of such a vaccine in inducing an immune response in a subject; and b) a method for the treatment and/or prophylaxis of ovarian cancer in a subject, or of vaccinating a subject against ovarian cancer which comprises the step of administering to the subject an effective amount of a CDCP1 polypeptide or nucleic acid, preferably as a vaccine.

Preferred features of each embodiment of the invention are as for each of the other embodiments mutatis mutandis. All publications, including but not limited to patents and patent applications cited in this specification are herein incorporated by reference as if each individual publication were specifically and individually indicated to be incorporated by reference herein as though fully set forth.

The invention will now be described with reference to the following examples, which are merely illustrative and should not in any way be construed as limiting the scope of the present invention.

FIG. 1: shows the amino acid (SEQ ID NO:1) sequence of a CDCP1 polypeptide. The tandem mass spectra are in bold, mass matches bold and underlined.

FIG. 2: shows a nucleic acid sequence (SEQ ID NO:2) encoding a CDCP1 polypeptide.

FIG. 3: shows tissue distribution of CDCP1 mRNA. Levels of mRNA in normal tissues and ovarian carcinoma cell lines and tissues were quantified by real time RT-PCR. mRNA levels are expressed as the number of copies $ng^{-1}$ cDNA. Samples CI06829T, CI06326T, CU01081T, CU06481T, CI00069T and CI05532T are ovary adenocarcinoma samples. Samples CI214T, CU9398T and CI6902T are derived from osteosarcoma. OV 90, SK OV3 and TOV 112D are human ovary adenocarcinoma cell lines.

EXAMPLE 1

Isolation of CDCP1 Protein from Tumour-Derived Cell Lines

Proteins in tumour-derived cell line membranes were separated by SDS-PAGE and analysed.

1a—Cell Culture

Human prostate, colorectal adenocarcinoma cells (HCT-15, HT-29, LoVo, LS174T, SW620 and SW948 cells), breast, liver, pancreatic and kidney (293 cells, an embryonic kidney cell line transformed by adenovirus DNA; 786-0 & ACHN cells, renal adenocarcinomas; A-498 & A-704 cells, renal carcinomas; Caki-2 cells, a renal clear cell carcinoma, and SW839 cells, a renal clear cell adenocarcinoma) were grown at 37° C. in a humidified atmosphere of 95% air and 5% carbon dioxide.

1b—Cell Fractionation and Plasma Membrane Generation

Purified membrane preparations were isolated from the cell lines. Adherent cells ($2 \times 10^8$) were washed three times with PBS and scraped using a plastic cell lifter. Cells were centrifuged at 1000×g for 5 min at 4° C. and the cell pellet was resuspended in homogenisation buffer (250 mM Sucrose, 10 mM HEPES, 1 mM EDTA, 1 mM Vanadate and 0.02% azide, protease inhibitors). Cells were fractionated using a ball bearing homogeniser (8.002 mm ball, HGM Lab equipment) until approximately 95% of cells were broken. Membranes were fractionated using the method described by Pasquali et al (Pasquali et al., 1999 *J. Chromatography* 722: pp 89-102). The fractionated cells were centrifuged at 3000×g for 10 min at 4° C. and the postnuclear supernatant was layered onto a 60% sucrose cushion and centrifuged at 100 000×g for 45 min. The membranes were collected using a pasteur pipette and layered on a preformed 15 to 60% sucrose gradient and spun at 100 000×g for 17 hrs. Proteins from the fractionated sucrose gradient were run on a 4-20% 1D gel (Novex) and subject to western blotting; those fractions containing alkaline phosphatase and transferrin immunoreactivity but not oxidoreductase II or calnexin immunoreactivity were pooled and represented the plasma membrane fraction.

1c—Preparation of Plasma Membrane Fractions for 1D-Gel Analysis

Plasma membrane fractions that had transferrin immunoreactivity but no oxidoreductase II or calnexin immunoreactivity were identified and pooled. This pool which represented the plasma membrane fraction was diluted at least four times with 10 mM HEPES, 1 mM EDTA 1 mM Vanadate, 0.02% Azide and added to a SW40 or SW60 tube and centrifuged at 100 000×g for 45 min with slow acceleration and deceleration. The supernatant was removed from the resulting membrane pellet and the pellet washed three times with PBS-CM. The membrane pellet was solubilised in 2% SDS in 63 mM TrisHCl, pH 7.4. A protein assay was performed followed by the addition of mercaptoethanol (2% final), glycerol (10%) and bromophenol blue (0.0025% final) was added. A final protein concentration of 1 microgram/microlitre was used for 1D-gel loading.

1d—1D-Gel Technology

Protein or membrane pellets were solubilised in 1D-sample buffer (approximately 1 mg/ml) and the mixture heated to 95° C. for 5 min.

Samples were separated using 1D-gel electrophoresis on pre-cast 8-16% gradient gels purchased from Bio-Rad (Bio-Rad Laboratories, Hemel Hempstead, UK). A sample containing 30-50 micrograms of the protein mixtures obtained from a detergent extract were applied to the stacking gel wells using a micro-pipette. A well containing molecular weight markers (10, 15, 25, 37, 50, 75, 100, 150 and 250 kDa) was included for calibration by interpolation of the separating gel after imaging. Separation of the proteins was performed by applying a current of 30 mA to the gel for approximately 5 hrs or until the bromophenol blue marker dye had reached the bottom of the gel.

After electrophoresis the gel plates were prised open, the gel placed in a tray of fixer (10% acetic acid, 40% ethanol, 50% water) and shaken overnight. The gel was then primed for 30 minutes by shaking in a primer solution (7.5% acetic acid, 0.05% SDS in Milli-Q water) followed by incubation with a fluorescent dye (0.06% OGS dye in 7.5% acetic acid) with shaking for 3 hrs. A preferred fluorescent dye is disclosed in U.S. Pat. No. 6,335,446. Sypro Red (Molecular Probes, Inc., Eugene, Oreg.) is a suitable alternative dye for this purpose.

A digital image of the stained gel was obtained by scanning on a Storm Scanner (Molecular Dynamics Inc, USA) in the blue fluorescence mode. The captured image was used to determine the area of the gel to excise for in-gel proteolysis.

1e—Recovery and Analysis of Selected Proteins

Each vertical lane of the gel was excised using a stainless steel scalpel blade. Proteins were processed using in-gel digestion with trypsin (Modified trypsin, Promega, Wis., USA) to generate tryptic digest peptides. Recovered samples were divided into two. Prior to MALDI analysis samples were desalted and concentrated using C18 Zip Tips™ (Millipore, Bedford, Mass.). Samples for tandem mass spectrometry were purified using a nano LC system (LC Packings, Amsterdam, The Netherlands) incorporating C18 SPE material. Recovered peptide pools were analysed by MALDI-TOF-mass spectrometry (Voyager STR, Applied Biosystems, Framingham, Mass.) using a 337 nm wavelength laser for desorption and the reflection mode of analysis. Pools were also analyzed by nano-LC tandem mass spectrometry (LC/MS/NIS) using a Micromass Quadrupole Time-of-Flight (Q-TOF) mass spectrometer (Micromass, Altrincham, UK). For partial amino acid sequencing and identification of cancer cell membrane proteins, uninterpreted tandem mass spectra of tryptic peptides were searched against a database of public domain proteins constructed of protein entries in the non-redundant database held by the National Centre for Biotechnology Information (NCBI) which is accessible at http://www.ncbi.nlm.nih.gov/ using the SEQUEST search program (Eng et al., 1994, *J. Am. Soc. Mass Spectrom.* 5:976-989), version v.C.1. Criteria for database identification included: the cleavage specificity of trypsin; the detection of a suite of a, b and y ions in peptides returned from the database, and a mass increment for all Cys residues to account for carbamidomethylation. Following identification of proteins through spectral-spectral correlation using the SEQUEST program, masses detected in MALDI-TOF mass spectra were assigned to tryptic digest peptides within the proteins identified. In cases where no amino acid sequences could be identified through searching with uninterpreted MS/MS spectra of tryptic digest peptides using the SEQUEST program, tandem mass spectra of the peptides were interpreted manually, using methods known in the art. (In the case of interpretation of low-energy fragmentation mass spectra of peptide ions see Gaskell et al., 1992, *Rapid Commun. Mass Spectrom.* 6:658-662). The method described in WO 02/21139 was also used to interpret mass spectra.

Seven tandem spectrum (shown in bold) and three mass matches (bold and underlined) were found to match the GenBank accession NM_022842 representing CDCP1 in the cancer cell lines (SEQ ID NO:1; FIG. 1).

EXAMPLE 2

Elevated Expression of CDCP1 mRNA in Ovarian Cancers Using Quantitative RT-PCR (Taqman) Analysis Tissue samples were from Ardais Corp. (Lexington, Mass.). Real time RT-PCR was used to quantitatively measure CDCP1 expression in ovarian tumour tissues and normal tissues. The primers used for PCR were as follows:

```
                                    (SEQ ID NO: 3)
Sense,      5'- tcacagaaaggtatccacgctg -3', (SEQ ID NO: 4)
Antisense,  5'- catcctctgcatcattgtactg -3'
```

Reactions containing 5 ng cDNA, SYBR green sequence detection reagents (PE Biosystems) and sense and antisense primers were assayed on an ABI7700 sequence detection system (PE Biosystems). The PCR conditions were 1 cycle at 50° C. for 2 min, 1 cycle at 95° C. for 10 min, and 40 cycles of 95° C. for 15 s, 65° C. for 1 min. The accumulation of PCR product was measured in real time as the increase in SYBR green fluorescence, and the data were analysed using the Sequence Detector program v1.6.3 (PE Biosystems). Standard curves relating initial template copy number to fluorescence and amplification cycle were generated using the amplified PCR product as a template, and were used to calculate CDCP1 copy number in each sample.

Relatively low expression levels of CDCP1 were seen in normal ovary tissue (FIG. 3). In contrast, levels of CDCP1 expression were greatly increased in 4/6 ovarian tumour samples and in ovarian adenocarcinoma cell lines relative to normal ovary (FIG. 3). These data indicate that CDCP1 is a target for therapeutic intervention in ovarian cancer.

EXAMPLE 3

Generation of an Anti-CDCP1 Polyclonal Antibody

Rats were immunised with a recombinant sequence(s) encoding the predicted extracellular domain of (CDCP1) comprising residues 30-667 of SEQ ID NO:1. Three immunisations resulted in a significant anti-CDCP1 response. Blood was harvested at this point and anti-CDCP1 polyclonal antibody prepared by affinity purification against recombinant CDCP1 protein using standard methodology.

EXAMPLE 4

Immunohistochemical Analysis of CDCP1 Protein Expression in Clinical Normal and Ovarian Cancer Tissues Immunohistochemistry was performed on a range of normal tissues and multiple ovarian cancer donor tissues using the polyclonal antibody of Example 3. The normal tissues were from Medical Solutions Plc, Nottingham, UK and included breast, liver, prostate, thyroid, spleen, duodenum, lung, ovary, heart, ileum, colon and pancreas. Ovarian tumour tissues were from Ardais Corp., MD.

Frozen normal and tumour tissue sections were thawed for 15 minutes at room temperature then fixed in cold acetone for 5 minutes. Endogenous peroxidase activity was quenched by a 5 minute room temperature incubation in peroxidase-blocking reagent (DakoCytomation), washed by immersing in tris-buffered saline (TBS), then blocked for 30 minutes at room temperature in serum-free protein block (DakoCytomation). Anti-CDCP1 polyclonal antibody (1 µg/ml in DakoCytomation antibody diluent) was then incubated on the tissues at room temperature for 1 hour followed by two washes in TBS for 5 minutes each. Tissue sections were then incubated with a biotin-conjugated secondary antibody (Biotin-SP-conjugated AffiniPure donkey anti-rat, Jackson ImmunoResearch) diluted at 1:200 (2.5 µg/ml in antibody diluent) for 1 hour. Slides were washed 3 times in TBS and the tissue incubated with Streptavidin-HRP (Jackson ImmunoResearch) diluted 1:500 (1 µg/ml in antibody diluent) for 30 minutes at room temperature, followed by three 5-minute washes in TBS. Antibody signal was achieved by a 5 minute incubation in the presence of 3,3'-diaminobenzidine substrate chromogen (DAB+, DakoCytomation) which results in a brown coloured precipitate at the antigen site. Sections were counter stained in haematoxylin (DakoCytomation) and mounted under glass cover slips using aqueous mounting medium (Faramount, DakoCytomation).

Weak CDCP1 expression only was seen in colon, ileum and pancreas; all the other normal tissues were negative. CDCP1 expression in 14 frozen ovarian cancer donor tissues (Ardais Corp, Md.) was also investigated. 65% of donors showed good tumour tissue staining with the clear cell (2/2) and endometrioid (2/3) subtypes showing the strongest staining (Table 1).

| Strength of staining; % tumour stained | Donor ID | Tumour Type | | % |
|---|---|---|---|---|
| +++; 100% | CU1993 | Clear cell | 2/2 | 36% |
| | CU6458 | Clear cell | | |
| | CI125 | Endometrioid | 2/3 | |
| | CU11119 | Endometrioid | | |
| | CU668 | Mucinous | 1/3 | |
| ++; 100% | CI7291 | Mucinous | | 22% |
| | CI19559 | Papillary Serous | | |
| | CU6850 | Serous | | |
| ++; 40% | CU6650 | Papillary Serous | | 7% |
| | CI13212 | Serous | | 35% |

-continued

| Strength of staining; % tumour stained | Donor ID | Tumour Type | % |
|---|---|---|---|
| +; >100% | CU5838 | Serous | |
| | CU6128 | Endometrioid | |
| − | CI19417 | Papillary Serous | |
| | CI13591 | Mucinous | |

(+++ = strong tumour staining, ++ = moderate staining, + = weak staining, − = no staining)

EXAMPLE 5

CDCP1 is Internalised on Anti-CDCP1 Antibody Binding to an Ovarian Cancer Cell Line Endogenously Expressing CDCP1

Ovarian cancer-derived OvCar3 cells were seeded at a density of $5 \times 10^4$ cells per chamber of an 8-well chamber slide and incubated as normal (37° C., 5% $CO_2$) for 24 hours. Media was removed and the cells washed carefully in cold Dulbecco's PBS (DPBS). 1 µg/ml anti-CDCP1 polyclonal antibodies (see Example 3) and isotype control antibody were prepared in 200 µl cold serum free DMEM/F12 media, added to their respective chambers and incubated at 4° C. for 20 mins. Cells were washed twice with DPBS and the 0 hr samples fixed in 4% paraformaldehyde (PFA) for 10 mins. Warmed media was added to the remaining chambers and the cells incubated for 30 mins, 1 and 2 hrs before fixation. After fixation the cells are washed twice in DPBS then blocked/permeabilised for 20 mins at room temperature (RT) in 0.1% saponin/5% donkey serum in DPBS. Biotinylated goat anti-rat IgG diluted 1:200 (10 µg/ml) in 5% donkey serum/PBS was then added for 1 hr at room temperature followed by three washes in DPBS. Extravidin-Cy3 (Sigma-Aldrich) diluted 1:500 in 0.1% saponin/5% donkey serum/PBS was added for 30 mins followed by three washes in PBS. The cells were then mounted in fluorescence enhancing mounting media (Dako-Cytomation, Ely, UK) and examined using a Leica Microsystems fluorescence microscope with ×63 oil immersion objective.

Results of these studies showed that within the first hour post addition of warmed media the CDCP1-antibody complex was predominantly plasma-membrane localized. However, after 2 hours there was clear evidence of internalization of the CDCP1-antibody complex with weak membrane staining and strong intracellular (endosomal) staining. These results indicate that CDCP1 is a suitable target for therapy of ovarian cancer using an antibody, most preferably using an antibody-dependent cytotoxic approach.

The invention claimed is:

1. A method for the treatment of ovarian cancer comprising administering a therapeutically effective amount of an anti-CDCP1 antibody which interacts with a CDCP1 polypeptide.

2. The method according to claim 1, wherein the antibody is monoclonal, polyclonal, chimeric, humanised or bispecific, or is conjugated to a therapeutic moiety, second antibody an antigen-binding fragment or thereof, an effector or reporter molecule, a cytotoxic agent or a cytokine.

3. The method according to claim 1, wherein the CDCP1 polypeptide
comprises or consists of the amino acid sequence of SEQ ID NO:1.

* * * * *

UNITED STATES PATENT AND TRADEMARK OFFICE
CERTIFICATE OF CORRECTION

| | | |
|---|---|---|
| PATENT NO. | : 8,263,071 B2 | Page 1 of 1 |
| APPLICATION NO. | : 12/587870 | |
| DATED | : September 11, 2012 | |
| INVENTOR(S) | : Burgess | |

It is certified that error appears in the above-identified patent and that said Letters Patent is hereby corrected as shown below:

In the Claims

Claim 2 is deleted and should read as follows:

2. The method according to claim 1, wherein the antibody is monoclonal, polyclonal, chimeric, humanised or bispecific, or is conjugated to a therapeutic moiety, detectable label, second antibody or a fragment thereof, an effector or reporter molecule, a cytotoxic agent or a cytokine.

Signed and Sealed this
Eleventh Day of February, 2014

Michelle K. Lee
*Deputy Director of the United States Patent and Trademark Office*

UNITED STATES PATENT AND TRADEMARK OFFICE
CERTIFICATE OF CORRECTION

PATENT NO. : 8,263,071 B2
APPLICATION NO. : 12/587870
DATED : September 11, 2012
INVENTOR(S) : Burgess Page 1 of 1

It is certified that error appears in the above-identified patent and that said Letters Patent is hereby corrected as shown below:

In the Claims

Column 39, lines 35-37, Claim 2 is deleted and should read as follows:

2. The method according to claim 1, wherein the antibody is monoclonal, polyclonal, chimeric, humanised or bispecific, or is conjugated to a therapeutic moiety, detectable label, second antibody or a fragment thereof, an effector or reporter molecule, a cytotoxic agent or a cytokine.

This certificate supersedes the Certificate of Correction issued February 11, 2014.

Signed and Sealed this
Eighteenth Day of March, 2014

Michelle K. Lee
*Deputy Director of the United States Patent and Trademark Office*